(12) United States Patent
Neumann

(10) Patent No.: US 12,073,296 B2
(45) Date of Patent: Aug. 27, 2024

(54) METHODS AND SYSTEMS FOR GENERATING PHYSICAL ACTIVITY SETS FOR A HUMAN SUBJECT

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 1007 days.

(21) Appl. No.: 17/032,066

(22) Filed: Sep. 25, 2020

(65) Prior Publication Data

US 2021/0162261 A1   Jun. 3, 2021

Related U.S. Application Data

(63) Continuation-in-part of application No. 16/699,400, filed on Nov. 29, 2019, now Pat. No. 10,857,426.

(51) Int. Cl.
*G06N 20/00*   (2019.01)
*A61B 5/11*   (2006.01)
(Continued)

(52) U.S. Cl.
CPC ......... *G06N 20/00* (2019.01); *A63B 24/0075* (2013.01); *A63B 71/0622* (2013.01);
(Continued)

(58) Field of Classification Search
CPC ...... G06N 20/00; G06N 7/01; A63B 24/0075; A63B 71/0622; A63B 2024/0065;
(Continued)

(56) References Cited

U.S. PATENT DOCUMENTS 9,474,934 B1   10/2016 Krueger et al.
9,704,412 B2   7/2017 Wells et al.
(Continued)

FOREIGN PATENT DOCUMENTS

WO   2019075185   4/2019

OTHER PUBLICATIONS

"Heart Rate Monitoring, Activity Recognition, and Recommendation for E-Coaching"; Pessemier & Martens; Sep. 2008; https://biblio.ugent.be/download/8572386/8572388.pdf.
(Continued)

*Primary Examiner* — Pierre E Elisca
(74) *Attorney, Agent, or Firm* — Caldwell Intellectual Property Law

(57) ABSTRACT

A system for generating physical activity sets for a human subject, the system comprising a computing device configured to detect a signal from a wearable fitness device, determine an activity profile using an activity machine-learning model and the signal, generate using the activity profile, at least a physical activity set, wherein generating further comprising classifying the activity profile with corresponding activity profile data from a plurality of human subjects, wherein the corresponding activity profile data correlates activity profile data to at least a physical activity set, training a fitness machine-learning model using the corresponding activity profile data, generating the at least a physical activity set as a function of the activity profile data and the fitness machine-learning model, and generate a presentation of the activity profile and the at least a physical activity set using a graphical user interface.

20 Claims, 9 Drawing Sheets

(51) Int. Cl.
    *A63B 24/00*     (2006.01)
    *A63B 71/06*     (2006.01)
    *G09B 19/00*     (2006.01)
    *G16H 10/20*     (2018.01)
    *G16H 20/30*     (2018.01)
    *G16H 40/67*     (2018.01)
    *G16H 50/70*     (2018.01)

(52) U.S. Cl.
    CPC ......... *G09B 19/0038* (2013.01); *G16H 10/20* (2018.01); *G16H 20/30* (2018.01); *G16H 40/67* (2018.01); *G16H 50/70* (2018.01); *A61B 5/1118* (2013.01); *A63B 2024/0065* (2013.01); *A63B 2071/0675* (2013.01); *A63B 2220/836* (2013.01)

(58) Field of Classification Search
    CPC ...... A63B 2071/0675; A63B 2220/836; G09B 19/0038; G16H 10/20; G16H 20/30; G16H 40/67; G16H 50/70; A61B 5/1118; A61B 5/02055; G06F 18/23213
    USPC .......................................................... 434/29
    See application file for complete search history.

(56) References Cited

U.S. PATENT DOCUMENTS

| | | |
|---|---|---|
| 9,848,823 B2 | 12/2017 | Raghuram et al. |
| 2015/0294595 A1 | 10/2015 | Hu et al. |
| 2016/0262693 A1 | 9/2016 | Sheon |
| 2017/0061817 A1 | 3/2017 | Mettler May |
| 2017/0100637 A1 | 4/2017 | Princen et al. |
| 2017/0266501 A1* | 9/2017 | Sanders .................. G06N 3/08 |
| 2018/0090229 A1* | 3/2018 | Sanyal ................ A61B 5/0024 |
| 2018/0133551 A1 | 5/2018 | Chang et al. |
| 2018/0330810 A1* | 11/2018 | Gamarnik .............. G16H 10/20 |
| 2018/0342323 A1* | 11/2018 | Shankar ................ G16H 10/60 |
| 2018/0361203 A1* | 12/2018 | Wang .................... G06N 20/00 |
| 2019/0209022 A1 | 7/2019 | Sobol et al. |

OTHER PUBLICATIONS

"Gymwatch Launches the First Fitness Tracker to Measure Both Strength and Motion and Offer Real-Time Feedback on Every Type of Exercise"; Business Wire; Nov. 11, 2014; https://www.businesswire.com/news/home/20141111006152/en/GYMWATCH-Launches-Fitness-Tracker-Measure-Strength-Motion.

\* cited by examiner

METHODS AND SYSTEMS FOR GENERATING PHYSICAL ACTIVITY SETS FOR A HUMAN SUBJECT

CROSS-REFERENCE TO RELATED APPLICATIONS

This application is a continuation-in-part of Non-provisional application Ser. No. 16/699,400 filed on Nov. 29, 2019 and entitled "METHODS AND SYSTEMS FOR GENERATING FITNESS RECOMMENDATIONS ACCORDING TO USER ACTIVITY PROFILES," the entirety of which is incorporated herein by reference.

FIELD OF THE INVENTION

The present invention generally relates to the field of machine-learning. In particular, the present invention is directed to methods and systems for generating physical activity sets for a human subject.

BACKGROUND

Adequate practice of exercises designed to enhance one's longevity can be challenging. Frequently, consumers are overloaded concerning a variety of fitness trends often involving expensive equipment and offering dubious potential for health benefit. Selection of exercises unique to human subjects on a microphysiological level remains to be seen.

SUMMARY OF THE DISCLOSURE

In an aspect, a system for generating physical activity sets for a human subject, the system including a computing device configured to detect a signal from the at least a sensor, determine an activity profile, wherein determining the activity profile includes generating an activity machine-learning model, wherein the activity machine-learning model is trained with training data that includes a plurality of entries and each entry correlates human subject signal to a plurality of human subject activity metrics, determining, using the activity machine-learning model and the signal, the activity profile, generating, using the activity profile, at least a physical activity set wherein generating at least a physical activity set includes classifying the activity profile with corresponding activity profile data from a plurality of human subjects, wherein the corresponding activity profile data correlates activity profile data to at least a physical activity set, training a fitness machine-learning model using the corresponding activity profile data, generating the at least a physical activity set as a function of the activity profile data and the fitness machine-learning model, and generate a presentation of the activity profile and the at least a physical activity set using a graphical user interface.

In an aspect, a method for generating physical activity sets for a human subject, the method including a computing device configured for detecting a signal from the at least a sensor, determining an activity profile, wherein determining the activity profile includes generating an activity machine-learning model, wherein the activity machine-learning model is trained with training data that includes a plurality of entries and each entry correlates human subject signal to a plurality of human subject activity metrics, determining, using the activity machine-learning model and the signal, the activity profile, generating, using the activity profile, at least a physical activity set wherein generating at least a physical activity set includes classifying the activity profile with corresponding activity profile data from a plurality of human subjects, wherein the corresponding activity profile data correlates activity profile data to at least a physical activity set, training a fitness machine-learning model using the corresponding activity profile data, generating the at least a physical activity set as a function of the activity profile data and the fitness machine-learning model, and generating a presentation of the activity profile and the at least a physical activity set using a graphical user interface.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating physical activity sets for human subjects according to activity profiles. In an embodiment, a computing device is configured to utilize signals from a wearable fitness device sensor of a human subject to train a machine-learning model to generate an activity profile of the subject. Computing device may use reactive computing to generate real-time updates to a human subject during activity, wherein real-time updates show changes in human subject physiology during activity. Computing device may use a machine-learning model to identify physical activities suitable to a human subject based on the activity profile. Computing device may utilize a machine-learning process to rank and filter physical activities based on the human subject data collected and analyzed by the computing device and the computing device is configured to generate a physical activity instruction set. In an embodiment, computing device may generate a presentation of the activity profile, the ranked physical activity set, and the physical activity instruction set via a graphical user interface.

As used herein, "human subject," is used to reference an individual who is intended to engage with the system and methods as described herein. Human subject, herein, may be used interchangeably with the term "subject." The subject is intended to be the individual with respect data, outputs, inputs, biological extraction, and the like, are directly connected with, and the individual to which the physical activities, fitness activities, and the like are directed to.

Figure 1:
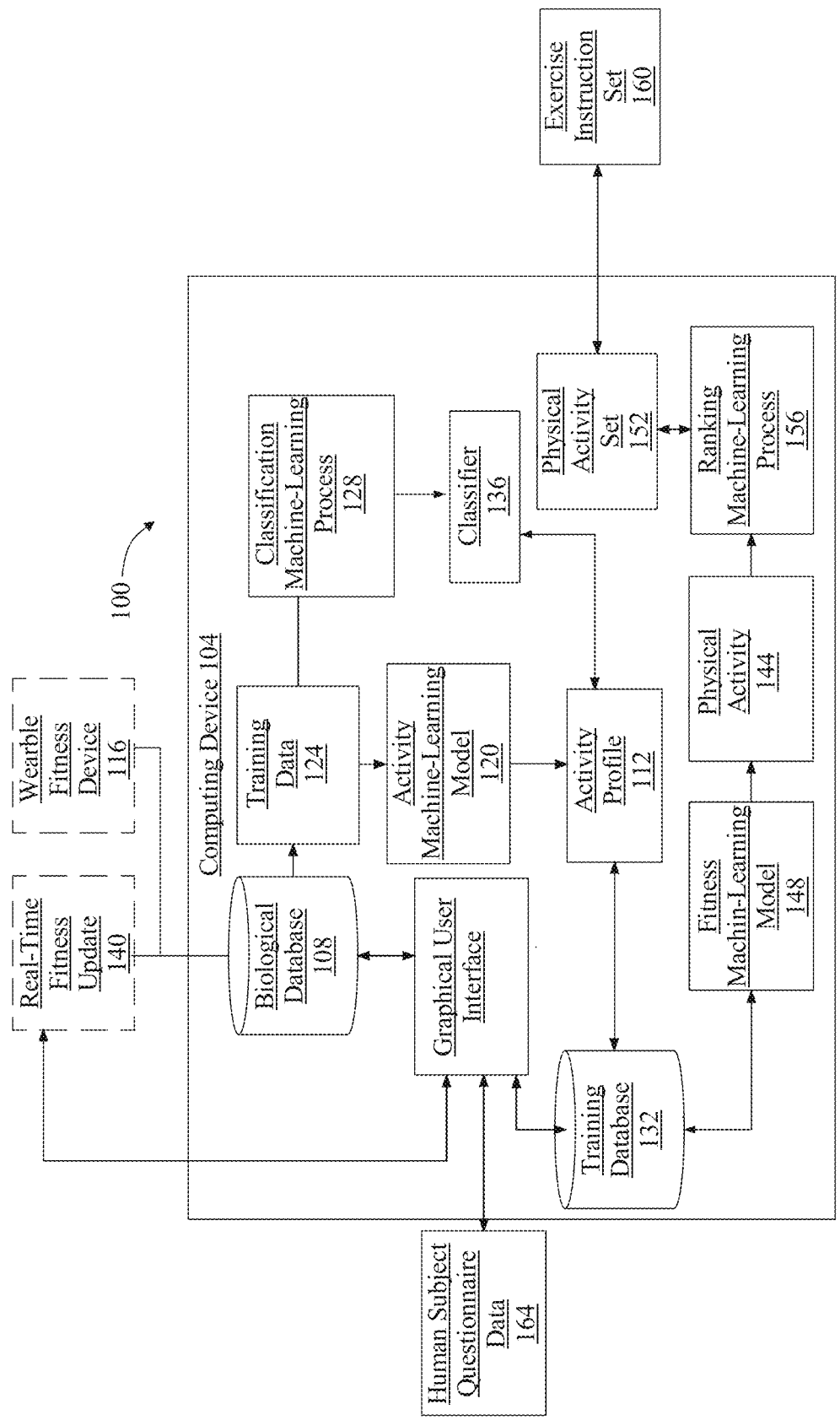
FIG. 1 is a block diagram illustrating an exemplary embodiment of a system for generating physical activity sets for a human subject.

Referring now to FIG. 1, an exemplary embodiment of a system 100 for generating physical activity sets for human subjects. System 100 includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently or may include two or more computing device 104 operating in concert, in parallel, sequentially or the like; two or more computing devices 104 may be included together in a single computing device 104 or in two or more computing devices 104. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices 104, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing devices 104 in a first location and a second computing device 104 or cluster of computing devices 104 in a second location. Computing device 104 may include one or more computing devices 104 dedicated to data storage, security, distribution of traffic for load balancing, and the like. Computing device 104 may distribute one or more computing tasks as described below across a plurality of computing devices 104 of computing device 104, which may operate in parallel, in series, redundantly, or in any other manner used for distribution of tasks or memory between computing devices 104. Computing device 104 may be implemented using a "shared nothing" architecture in which data is cached at the worker; in an embodiment, this may enable scalability of system 100 and/or computing device 104.

Still referring to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 is configured to retrieve from a biological database an activity profile. Biological database 108 may be implemented, without limitation, as a relational database, a key-value retrieval datastore such as a NOSQL database, or any other format or structure for use as a datastore that a person skilled in the art would recognize as suitable upon review of the entirety of this disclosure, as described in further detail below. Biological database 108 may be configured to store one or more activity profiles. An "activity profile" as used in this disclosure, is a set of one or more data entries describing exercise, activity, actions, efforts, or any other physical tasks a human subject may perform and includes activity metrics. An activity profile 112 may include at least an element of biological extraction data as it pertains to the human subject data. A "biological extraction" as used in this disclosure, is at least an element of data pertaining to human subject body measurements, including physiological, biological, chemical, and physical parameters.

Biological extraction data may refer to systolic and diastolic blood pressure, resting heart rate, and heart rate plasticity to activity, VO2 max and maximal oxygen uptake capacity and changes with activity, bodily sensitivity to elevation during exercise, blood chemistry including electrolytes, glucose and kidney function, aspartate aminotransferase (AST) and alanine aminotransferase (ALT) enzyme content, creatine kinase (CK) levels, sleep frequency, duration, and quality, muscular endurance, body mass index (BMI), among other categories of physiological, biological, chemical, and physical data. A "body measurement" as used in this disclosure, includes a measurable indicator of the severity, absence, and/or presence of a disease state from the biological extraction data of a human subject. A "disease state" as used in this disclosure, includes any harmful deviation from the normal structural and/or function state of a human subject. A disease state may include any medical condition and may be associated with specific symptoms, signs, or any other clinical manifestation. A disease state may be classified into different types including infectious diseases such as a viral, parasitic, and/or bacterial infection, deficiency diseases such as anemia, chronic or acute nutritional deficiency, hereditary diseases such as sickle cell anemia, and/or physiological diseases such as sleep deprivation, overtraining, and the like. For instance and without limitation, internal dysfunction of the immune system may produce a variety of different diseases including immunodeficiency, hypersensitivity, allergies, and/or autoimmune disorders that may be observed in the biological extraction data as analyzed by a computing device from signals from physiological sensors.

With continued reference to FIG. 1, a signal from the at least a sensor includes a wearable fitness device. As used in this disclosure, "signal" is a signal containing data indicative of a human subject's physiological state; physiological state may be evaluated by the computing device 104 with regard to one or more measures of health of a human subject's body, one or more systems within a human subject's body such as a circulatory system, a digestive system, a nervous system, or the like, one or more organs within a person's body, and/or any other subdivision of a person's body useful for diagnostic or prognostic purposes. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, electrolytes, AST and ALT content, blood glucose, CK levels, and/or mean corpuscular hemoglobin concentration may be recognized as useful for identifying various conditions such as dehydration, high and/or low testosterone, nutrient deficiencies, kidney dysfunction, chronic inflammation, anemia, overtraining, blood loss, and/or acute injury.

With continued reference to FIG. 1, physiological state data may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data may include, without limitation, immune function data such as Interleukine-6 (IL-6), TNF-alpha, systemic inflammatory cytokines, and the like.

Continuing to refer to FIG. 1, physiological state data may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data may include measures of glucose metabolism such as fasting glucose levels and/or hemoglobin A1-C(HbA1c) levels. Physiological state data may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data may include measures of estimated glomerular filtration rate (eGFR). Physiological state data may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data may include antinuclear antibody levels. Physiological state data may include aluminum levels. Physiological state data may include arsenic levels. Physiological state data may include levels of fibrinogen, plasma cystatin C, and/or brain natriuretic peptide.

Continuing to refer to FIG. 1, physiological state data may include measures of lung function such as forced expiratory volume, one second (FEV-1) which measures how much air can be exhaled in one second following a deep inhalation, forced vital capacity (FVC), which measures the volume of air that may be contained in the lungs. Physiological state data may include a measurement blood pressure, including without limitation systolic and diastolic blood pressure. Physiological state data may include a measure of waist circumference. Physiological state data may include body mass index (BMI). Physiological state data may include one or more measures of bone mass and/or density such as dual-energy x-ray absorptiometry. Physiological state data may include one or more measures of muscle mass. Physiological state data may include one or more measures of physical capability such as without limitation measures of grip strength, evaluations of standing balance, evaluations of gait speed, pegboard tests, timed up and go tests, and/or chair rising tests.

Still viewing FIG. 1, physiological state data may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data may include one or more evaluations of sensory ability, including measures of audition, vision, olfaction, gustation, vestibular function and pain.

Continuing to refer to FIG. 1, physiological state data may include psychological data. Psychological data may include any data generated using psychological, neuro-psychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices; for instance, user patterns of purchases, including electronic purchases, communication such as via chat-rooms or the like, any textual, image, video, and/or data produced by the subject, any textual image, video and/or other data depicting and/or describing the subject, or the like. Any psychological data and/or data used to generate psychological data may be analyzed using machine-learning and/or language processing modules as described in this disclosure.

Still referring to FIG. 1, physiological state data may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data may include proteomic data, which as used herein is data describing all proteins produced and/or modified by an organism, colony of organisms, or system of organisms, and/or a subset thereof. Physiological state data may include data concerning a microbiome of a person, which as used herein includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data of a person, and/or on prognostic labels and/or ameliorative processes as described in further detail below.

With continuing reference to FIG. 1, physiological state data may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Physiological state data may include any physiological state data, as described above, describing any multicellular organism living in or on a person including any parasitic and/or symbiotic organisms living in or on the persons; non-limiting examples may include mites, nematodes, flatworms, or the like. Examples of physiological state data described in this disclosure are presented for illustrative purposes only and are not meant to be exhaustive.

With continued reference to FIG. 1, physiological data may include, without limitation any result of any medical test, physiological assessment, cognitive assessment, psychological assessment, or the like. System 100 may receive at least a physiological data from one or more other devices after performance; system 100 may alternatively or additionally perform one or more assessments and/or tests to obtain at least a physiological data, and/or one or more portions thereof, on system 100. For instance, at least physiological data may include or more entries by a user in a form or similar graphical user interface object; one or more entries may include, without limitation, user responses to questions on a psychological, behavioral, personality, or cognitive test. For instance, at least a server 104 may present to user a set of assessment questions designed or intended to evaluate a current state of mind of the user, a current psychological state of the user, a personality trait of the user, or the like; at least a server 104 may provide user-entered responses to such questions directly as at least a physiological data and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

With continued reference to FIG. 1, assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor. An informed advisor may include any medical professional who may assist and/or participate in the medical treatment of a user. An informed advisor may include a medical doctor, nurse, physician assistant, pharmacist, yoga instructor, nutritionist, spiritual healer, meditation teacher, fitness coach, health coach, life coach, and the like.

With continued reference to FIG. 1, physiological data may include data describing one or more test results, including results of mobility tests, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of at least a physiological sample consistent with this disclosure.

With continued reference to FIG. 1, physiological data may include one or more user body measurements, including for instance, and without limitation, any other biological extraction categories, tests, and the like, as described in U.S. Nonprovisional application Ser. No. 16/886,647 filed on May 28, 2020, and entitled "METHODS AND SYSTEMS FOR DETERMINING A PLURALITY OF BIOLOGICAL OUTCOMES USING A PLURALITY OF DIMENSIONS OF BIOLOGICAL EXTRACTION DATA AND ARTIFICIAL INTELLIGENCE," the entirety of which is incorporated herein by reference.

With continued reference to FIG. 1, physiological data may be obtained from a wearable sensor. A sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmographic equipment, or the like. A sensor may include any electromagnetic sensor, including without limitation electroencephalographic sensors, magnetoencephalographic sensors, electrocardiographic sensors, electromyographic sensors, or the like. A sensor may include a temperature sensor. A sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate, or the like. A sensor may detect bioimpedance of a subject including as it pertains to swelling, inflammation, hydrated state, and the like. A sensor may detect any hematological parameter including blood oxygen level, pulse rate, heart rate, pulse rhythm, blood sugar, and/or blood pressure. A sensor may be configured to detect internal and/or external biomarkers and/or readings. A sensor may be a part of system 100 or may be a separate device in communication with system 100, such as in a wearable fitness device. Persons skilled in the art, upon review of this disclosure in its entirety, will be aware of the various types of sensors which may collect signals of the physiological data described above.

With continued reference to FIG. 1, at least a wearable fitness device includes a sensor. A "wearable fitness device" as used in this disclosure, is a device that includes at least one sensor and may be utilized to collect and transmit a signal during a fitness activity. A wearable fitness device 116 is able to transmit a signal during fitness activity using a variety of methods, for instance with without limitation, by utilizing wearable adhesive sensors that attach to the skin, silver/silver chloride traces in compression garments, textile band electrodes, and the like, as a wearable sensor. Wearable fitness device may contain flexible and/or disposable type sensors that are applied in a manner similar to how medical devices for monitoring athletes in sports physiology studies, diabetes monitoring, heart monitoring by electrocardiogram (ECG/EKG), and the like. A device utilized to obtain a biological extraction may include any design of sensor, such as a fingerpick device utilized to obtain a blood sample and/or wearable singer sensor such as used for blood oxygenation measurements, an imaging device such as a computed tomography (CT) machine, a magnetic resonance imaging (MRI) machine, a needle, a collection tube utilized to collect a fluid or tissue sample such as a salivary sample or a stool sample, an optical image machine such as a camera or scanner, a hearing aid, headphone, headband, earring, watch, belt, socks, or other wearable sensor used for instance to determine calories burned, pedometer, and the like. Wearable fitness device 116 may include any device suitable for use with a remote device, as described in further detail below. In an embodiment, wearable fitness device 116 may be contained within remote device and/or contain a computing device.

With continued reference to FIG. 1, an activity profile 112 includes at least an element of human subject data. "Human subject data" as used in this disclosure, is data describing a physical activity the subject may have been engaged in either before, during, or after collection of a signal. "Activity" as used in this disclosure, includes any action that requires physical effort which may be performed to maintain, sustain, and/or improve one's health. Activity may include movement that a user may engage upon such as walking around subject's house, shoveling snow on subject's driveway, performing movement at a gym such as by exercising on a machine such as a treadmill or Stairmaster, participating in a group exercise class, performing a meditation sequence, practicing a yoga sequence, lifting weights, performing one or more exercise routines, taking a leisurely stroll, performing a series of stretches, and the like. Activity may include subconscious movement such as one's body movements while sleeping that include rolling from side to side while sleeping. Activity may include one or more exertions such as folding laundry, performing housework, cleaning dishes, dusting, carrying groceries, and the like. User activity data may include a description of one or more activities that a user engages in either before, during, or after collection of a signal. For instance and without limitation, human subject data may indicate a biological extraction such as a fasting blood glucose level which was obtained after a subject swam three miles. In yet another non-limiting example, human subject data may include that a biological extraction such as user's heart rate that was monitored while user participated in a spinning class. In yet another non-limiting example, human subject data may include a description of a yoga sequence user practiced after providing a stool sample.

With continued reference to FIG. 1, computing device 104 is configured to determine an activity profile 112, wherein determining may include generating an activity machine-learning model trained with training data that includes a plurality of entries and each entry correlates human subject signal to a plurality of human subject activity metrics. An activity machine-learning model may be generated using a machine-learning module performing any machine-learning algorithm as described herein. Activity machine-learning model 120 may be generated by training using training data 124, wherein the training data 124 includes a plurality of entries wherein each entry correlates human subject signal, such as signals measuring any of the above physiological categories, to a plurality of human subject activity metrics. Training data may originate from subjects performing an activity and the corresponding signals associated with the activity. Training data may be used to generate an activity metric. An "activity metric," as used in this disclosure, is a numerical value, function, matrix, vector, polar coordinate, or any other qualitative and/or quantitative indication of activity. In non-limiting illustrative examples, an activity metric may include a value that describes a human subject's overall fitness, which may be represented for instance by a percentile for subjects with similar biological extraction data. In further non-limiting illustrative examples, an activity metric may be a value that describes a subject's proficiency in various physical activities such as skiing, biking, hiking, the sport of weightlifting, and the like, which may be determined from training data from a user preforming one of said activities. In such an example, the activity machine-learning model 120 may train with data that relates a human subject's performance at weightlifting such as a Sinclair coefficients, which takes the relative maximal force produced in the snatch and clean and jerk exercises relative to the subject's body weight and determine an activity metric which is a qualitative measure of proficiency on a scale from novice, beginner, intermediate, advanced, elite, and world class, accompanied by a quantitative value which is the Sinclair score. In doing so, the trained activity machine-learning model 120 may translate signal data, such as force-speed signals collected during performing a snatch and clean and jerk weightlifting exercise and translate this data into proficiency in the sport of weightlifting to more closely tailor a physical activity instruction set, as described in further detail below.

Continuing in referring to FIG. 1, computing device may be configured to classify, using a classification machine-learning process, the signal to at least an element of human subject data. Classification machine-learning process may include any machine-learning algorithm that a machine-learning module may perform, as described in further detail below. Classification machine-learning process 128 may accept an input of a plurality of signals and generate an output that is a classifier, which assigns the signal data to categories of human subject data, as described above. Additionally, training data 124 may include classified signal data, wherein the signal data is classified to a plurality of activity metric categories. Training data, as used in this disclosure, is data containing correlations that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by computing device 104 may correlate any input data as described in this disclosure to any output data as described in this disclosure.

With continued reference to FIG. 1, "training data" as used in this disclosure, includes training data that includes a plurality of data entries each data entry containing activity profiles and correlated fitness profiles. Training data 124 and/or elements thereof may be entered by one or more users including for example, by one or more experts from remote device 204. Experts may include one or more physicians, fitness trainers, experts in exercise and the like who may contain one or more credentials that may certify them as an expert. Credentials may include one or more licenses such as a medical license or a certified fitness coach license. Credentials may include one or more board certifications such as aa certified personal trainer, a certified group exercise instructor, a certified exercise physiologist, a certified medical exercise specialist, a certification from an organization relating to exercise such as the American College of Sports Medicine and the like. Credentials may include a particular field of experience and practice such as a sports medicine doctor, orthopedic doctor, physiatrist, and the like. Credentials may include publications in top leading medical journals, newspapers, and articles. Credentials may include participation in one or more clinical trials.

With continued reference to FIG. 1, training data 124 includes a plurality of human subject signals correlated to a plurality of human subject activity metrics for determining an activity profile 112. An activity profile 112 may include a description of one or more physical activities that a human subject classified to an activity profile 112 is expected to be able to perform. An activity profile 112 may include a description of one or more target ranges, reference ranges, usual responses, and/or findings that a biological extraction should fall within for a subject with a certain activity profile 112. An activity profile 112 may include a selection of one or more training sets that may be relevant for a subject who may be classified to an activity profile 112. Relevant training sets pertaining to one or more activity profiles 112 may be stored within a training database 132. Training database 132 may include any data structure suitable for use as biological database 108, as described above.

With continued reference to FIG. 1, computing device 104 may generate classifier 136 using a classification machine-learning process 128. Computing device 104 may derive a classifier 136, for instance from training data, a model known as a "classifier" for sorting inputs into categories or bins of data. Classification machine-learning model may "learn" which categories can be derived into such models, for instance as a plurality of signals may correlate to human subject data, as described above. Classifier 136 may include any classifier as described herein. Classification may be performed using, without limitation, using linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, computing device 104 may be configured to generate classifier 136 using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)÷P(B), where P(AB) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate classifier 136 using a K-nearest neighbors (KNN) algorithm. A "K-nearest neighbors algorithm" as used in this disclosure, includes a classification method that utilizes feature similarity to analyze how closely out-of-sample features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\sum_{i=0}^{n}a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values. As a non-limiting example, K-nearest neighbors algorithm may be configured to classify an input vector including an activity profile 112, to clusters representing fitness profiles.

With continued reference to FIG. 1, generating classifier 136 by computing device 104 may include extracting from a activity profile 112 an activity descriptor relating to a biological extraction and inputting the biological extraction and the activity descriptor relating to the biological extraction into the classifier 136. An "activity descriptor" as used in this disclosure, includes a description of one or more activities that a user has engaged in. An activity descriptor may include a description of any activity that a user may practice, participate in, and/or engage in. Activity descriptor may include any activity that may not necessarily have been practiced or performed immediately before, during, or after a biological extraction. For example, an activity descriptor may include a description of a rock-climbing class user participates in three days each week, but which user was not participating in when user's blood was drawn to check user's hemoglobin levels. For instance and without limitation, computing device 104 may extract from an activity profile 112 an activity descriptor such as a descriptor of a spinning class that user was engaged in while user's temperature was measured. In such an instance, the spinning class that the user participated in while user obtained temperature readings may be input by computing device 104 into the classifier 136 to generate an output that includes a fitness profile.

Generating classifier 136 may include retrieving by the computing device 104 a plurality of chronological user biological extractions from biological database 108. "Chronological biological extractions" as used in this disclosure, includes a series of two or more user biological extractions obtained at two or more different points in time. Chronological biological extractions may include two or more measurements of the same biological extraction and/or two or more measurements of two or more different biological extractions. Chronologically obtained biological extractions may include biological extractions obtained at two different points in time which may include two or more biological extractions obtained immediately after one another, or after the passage of a certain interval of time such as a nanosecond, millisecond, second, minute, hour, day, week, month, year and the like. Computing device 104 classifies a plurality of chronological user biological extractions to each contain a classification label. A "classification label" as used in this disclosure, includes a label that indicates whether an input belongs to a particular class or not. A class may include any output generated by a classification machine-learning process 128. Classification machine-learning process 128 may include any of the classification machine-learning algorithms, as described herein. Computing device 104 may generate classification labels that may indicate whether a particular biological extraction is within normal limits or not within normal limits. "Normal limits" as used in this disclosure, include a set of upper and lower limits given a range value for a particular biological extraction. Normal limits may include a classification label that indicates whether a particular biological extraction contains normal or abnormal findings such as when a biological extraction may include a particular imaging scan such as an MRI or CT scan. Normal limits may be generated based on expert input, including any of the expert input as described above. Normal limits may be generated based on factors that include sex, age, race, medical history, general health and the like. Normal limits may be generated based on one or more third parties that may analyzed a particular biological extraction such as a particular laboratory that may analyze a urine sample may have certain established normal limits while a particular laboratory that may analyze a blood sample may have certain established normal limits. Chronological biological extractions that contain a classification label may indicating if a biological extraction is within normal limits or not within normal limits may then be input into classifier 136.

Continuing in reference to FIG. 1, computing device 104 may be configured to provide a real-time fitness update during a human subject activity using reactive computing, wherein the real-time fitness update is provided as a change in an element of human subject data of a human subject during collection of the signal. A "real-time fitness update," as used in this disclosure is an update provided to the subject in real-time, as the subject is performing an activity, wherein the fitness update is a change in an element of human subject data as determined from the signal collected during performance of the activity. In non-limiting illustrative examples, a real-time fitness update 140 may be that a subject's systolic and/or diastolic blood pressure increases by 50% during a particular exercise, which may or may not represent significant risk to the subject. In such an example, a subject may be notified by this spike in blood pressure as a function of completing the exercise due to the real-time fitness update 140 that is provided.

Continuing in reference to FIG. 1, reactive computing as used in this disclosure is a declarative programming paradigm that is concerned with data streams and the propagation of change in that data over sampled time period. Reactive computing may also be referred to as "reactive programming." Reactive computing may be used to iterative sample data inputs and, according to an internal "clock", generate iterative outputs in real-time, as the input data is collected. As used in this disclosure, input data may be a plurality of signals, as detected by at least a sensor and transmitted to the computing device 104. Computing device 104 may be configured, using reactive computing, to express static (such as arrays) and/or dynamic (such as event emitters) "data streams" with relative ease, and also communicate an inferred dependence within the associated "execution model" which facilitate the automatic propagation of the changed data flow. For instance, computing device 104 may be configured to employ a trained activity machine-learning model 120, which described a mathematical relationship between a particular signal to a particular human subject datum as the "execution model" to automatically propagate outputs form the incoming signal data.

Reactive computing may be simply expressed as a:=b+c wherein a is automatically updated whenever the values of b or c change, without the program having to re-execute the statement a:=b+c to determine the presently assigned value of a. Reactive computing used herein may be "model-view-controller" (MVC) architecture, wherein reactive programming can facilitate changes in an underlying model that are reflected automatically in an associated view. For instance, a trained activity machine-learning model, which can correlate signals to human subject activity metrics, wherein human subject activity metrics may be correlated to human subject data, including biological extraction data. Reactive computing may be performed by the computing device using reactive extensions, such as RxJs, RxJAva, RxPy, RxSwift, and other APIs. Reactive computing may be implemented using any type of change propagation algorithm, such as a pull, push, and/or push-pull type approach to data propagation. Reactive computing may be any object-oriented reactive programming (OORP), functional reactive programming (FRP), or the like. Reactive programming may be implemented using for instance rule-based reactive programming languages such as through using relation algebra with Ampersand, Elm, and/or Observable. Persons skilled in the art, upon review of this disclosure in its entirety, will be aware of the various ways in which to implement reactive computing to sample signals during subject activity and provide fitness updates in real-time.

Continuing in reference to FIG. 1, computing device 104 providing the real-time fitness updates 140 may store the real-time fitness updates 140 in a database. A database may be a biological database 108, as described above. Real-time fitness updates 140 may be stored and/or retrieved by computing device 104 to provide to a user updated activity profiles 112, human subject data, and the like. A user may access the data stored in the biological database 108 via a remote device, as described in further detail below.

With continued reference to FIG. 1, computing device 104 is configured to generate using the activity profile 112 a physical activity. "Physical activity" as used in this disclosure, is a suggested exercise, fitness action, and/or effort a subject may perform. Physical activities 144 may include exercise activities such as hiking, biking, swimming, weightlifting, meditation, yoga, Pilates, martial arts, or any other physical activity. Physical activity 144 may include different groups of exercises such as cardiovascular activities, strength and toning activities, meditative activities, relaxing activities, and the like. Physical activity 144 may include specific implementation details that contain information describing duration, frequency, periodicity concerning when a subject is advised to practice a particular exercise, including magnitude and intensity regarding the exertion a subject should practice a particular exercise at, and the like. For instance in non-limiting illustrative example, physical activity 144 may include a suggestion that includes a low-impact cardiovascular exercises such as swimming 1500 meters two days each week and practicing yoga for one-hour periods, three days each week at a moderate intensity. In yet another non-limiting example, physical activity 144 may include a recommendation that includes engaging in all cardiovascular activities for a total of 150 minutes but stopping in the event a subject's real-time fitness update 140 indicates a heart rate above 200 beats per minute during exercise.

With continued reference to FIG. 1, computing device 104 may generate an activity training set from training database 132. Activity training set may be selected by classifying an activity profile 112 to contain an activity classification label pertaining to a particular activity level. An activity classification label may include any classification label, as described above. Activity classification label may be generated using any of the classification labels as described above. In non-limiting exemplary embodiments, activity level may indicate if an activity profile 112 indicates a beginner activity level, such as a subject who may be new to practicing any level of fitness; activity level may indicate an intermediate activity level such as a subject who may routinely engage in activity but who is not an expert and who may still be capable of achieving higher levels of fitness or who may be able to engage in more and/or greater fitness levels; activity level may include an accelerated activity level such as a user who habitually engages in activity, and so on. Activity levels may also indicate particular types of activities that a particular activity profile 112 may engage in. For example, activity level may indicate cardiovascular activities, stretching activities, running activities, sprinting activities, marathon activities, weightlifting activities, high-impact activities, thrill-seeking activities, and the like. One or more activity classification labels may be generated based on expert input, including any of the expert input as described above. Computing device 104 may select an activity training set as a function of an activity classification label, for instance and without limitation, by using a classifier 136 generated by classification machine-learning process 128. In an embodiment, activity training set 148 may be organized and stored within training database 132 according to activity level. Computing device 104 may select an activity training set 148 that matches an activity classification label.

Continuing in reference to FIG. 1, computing device 104 may classify an activity profile 112 with corresponding activity profile 112 data from a plurality of human subjects, wherein the corresponding activity profile 112 data correlates activity profile 112 data to at least a physical activity set, and train a fitness machine-learning model using the corresponding activity profile 112 data. As used herein, "activity profile data" is data from and/or of activities profiles, including activity metrics, types of activities, times spend performing activities, proficiency at activities, and/or any other data that may be contained in an activity profile 112. A fitness machine-learning model may be any machine-learning model and/or algorithm performed by a machine-learning module, as described in further detail below. Fitness machine-learning model 148 may be generated using activity training set from the training database 132, as described above, corresponding to activity profile 112 data, for instance how a subject's activity profile 112 relates to their conditioning, proficiency, preferred fitness methods, and the like. The trained fitness machine-learning model 148 may then generate a physical activity set, wherein a physical activity set may include a plurality of physical activities 144 as generated as an output of the trained fitness machine-learning model 148.

With continued reference to FIG. 1, computing device 104 may generate a fitness machine-learning model 148 and a physical activity set using a fitness machine-learning model 148. Fitness machine-learning model 148 may be a feature learning algorithm. Feature learning algorithm inputs fitness profiles and outputs recommended exercise. A "feature learning model" as used herein, includes any machine-learning model as described herein. A feature learning model may include performing a series of one or more calculations, algorithms, and/or equations. A feature learning model may be generated using one or more feature learning algorithms. A "feature learning algorithm," as used herein, is a machine-learning algorithm that identifies associations between elements of data in a training data set, where particular outputs and/or inputs are not specified. For instance, and without limitation, a feature learning algorithm may detect co-occurrences of sets of fitness profiles, as defined above, with each other and with recommended exercise. As a non-limiting example, feature learning algorithm may detect co-occurrences of fitness profiles, as defined above, with each other and with cardiovascular exercise. Feature learning algorithm may include supervised feature learning algorithms that may be learned using labeled training data. For example, supervised feature learning algorithm may include supervised neural networks, multilayer perceptron, and/or supervised dictionary learning. Feature learning algorithm may include unsupervised machine learning algorithms that may be learned using unlabeled training data. Unsupervised feature learning algorithm may include k-means clustering, principal component analysis, local linear embedding, intendent component analysis, unsupervised dictionary learning, restricted Boltzmann machine, and/or autoencoder. Computing device 104 may perform a feature learning algorithm by dividing fitness profiles into various sub-combinations of such data to create fitness profile data sets, and evaluate which fitness datasets tend to co-occur with other fitness profile data sets, and recommended exercise; for instance, where fitness profile data includes cardiovascular exercise, computing device 104 may divide each exercise into individual data sets to identify which individual exercises and/or combinations thereof tend to co-occur with which other individual exercises, fitness profiles, and/or recommended exercise. In an embodiment, feature learning algorithm may perform clustering of data; for instance, a number of clusters into which data from training data sets may be sorted using feature learning may be set as a number of recommended exercises.

Continuing refer to FIG. 1, a feature learning and/or clustering algorithm may be implemented, as a non-limiting example, using a k-means clustering algorithm. A "k-means clustering algorithm" as used in this disclosure, includes cluster analysis that partitions n observations or unclassified cluster data entries into k clusters in which each observation or unclassified cluster data entry belongs to the cluster with the nearest mean, using, for instance behavioral training set as described above. "Cluster analysis" as used in this disclosure, includes grouping a set of observations or data entries in way that observations or data entries in the same group or cluster are more like each other than to those in other groups or clusters. Cluster analysis may be performed by various cluster models that include connectivity models such as hierarchical clustering, centroid models such as k-means, distribution models such as multivariate normal distribution, density models such as density-based spatial clustering of applications with nose (DBSCAN) and ordering points to identify the clustering structure (OPTICS), subspace models such as biclustering, group models, graph-based models such as a clique, signed graph models, neural models, and the like. Cluster analysis may include hard clustering whereby each observation or unclassified cluster data entry belongs to a cluster or not. Cluster analysis may include soft clustering or fuzzy clustering whereby each observation or unclassified cluster data entry belongs to each cluster to a certain degree such as for example a likelihood of belonging to a cluster; for instance, and without limitation, a fuzzy clustering algorithm may be used to identify clustering of gene combinations with multiple disease states, and vice versa. Cluster analysis may include strict partitioning clustering whereby each observation or unclassified cluster data entry belongs to exactly one cluster. Cluster analysis may include strict partitioning clustering with outliers whereby observations or unclassified cluster data entries may belong to no cluster and may be considered outliers. Cluster analysis may include overlapping clustering whereby observations or unclassified cluster data entries may belong to more than one cluster. Cluster analysis may include hierarchical clustering whereby observations or unclassified cluster data entries that belong to a child cluster also belong to a parent cluster.

With continued reference to FIG. 1, computing device 104 may generate a k-means clustering algorithm receiving unclassified fitness profile data and/or combinations thereof as inputs and outputs a definite number of classified data entry cluster wherein the data entry clusters each contain cluster data entries each containing recommended exercise. K-means algorithm may select a specific number of groups or clusters to output, identified by a variable "k." Generating a k-means clustering algorithm includes assigning inputs containing unclassified data to a "k-group" or "k-cluster" based on feature similarity. Centroids of k-groups or k-clusters may be utilized to generate classified data entry cluster. K-means clustering algorithm may select and/or be provided "k" variable by calculating k-means clustering algorithm for a range of k values and comparing results. K-means clustering algorithm may compare results across different values of k as the mean distance between cluster data entries and cluster centroid. K-means clustering algorithm may calculate mean distance to a centroid as a function of k value, and the location of where the rate of decrease starts to sharply shift, this may be utilized to select a k value. Centroids of k-groups or k-cluster include a collection of feature values which are utilized to classify data entry clusters containing cluster data entries. K-means clustering algorithm may act to classify a given fitness profile to one or more recommended exercise, enabling computing device 104 to identify.

With continued reference to FIG. 1, generating a k-means clustering algorithm may include generating initial estimates for k centroids which may be randomly generated or randomly selected from unclassified data input. K centroids may be utilized to define one or more clusters. K-means clustering algorithm may assign unclassified data to one or more k-centroids based on the squared Euclidean distance by first performing a data assigned step of unclassified data. K-means clustering algorithm may assign unclassified data to its nearest centroid based on the collection of centroids ci of centroids in set C. Unclassified data may be assigned to a cluster based on $\text{argmin}_{c_i \exists c} \text{dist}(c_i, x)^2$, where argmin includes argument of the minimum, ci includes a collection of centroids in a set C, and dist includes standard Euclidean distance. K-means clustering module may then recompute centroids by taking mean of all cluster data entries assigned to a centroid's cluster. This may be calculated based on $c_i = 1/|S_i| \Sigma x_i \exists S_i^{x_i}$. K-means clustering algorithm may continue to repeat these calculations until a stopping criterion has been satisfied such as when cluster data entries do not change clusters, the sum of the distances have been minimized, and/or some maximum number of iterations has been reached.

Still referring to FIG. 1, k-means clustering algorithm may be configured to calculate a degree of similarity index value. A "degree of similarity index value" as used in this disclosure, includes a distance measurement indicating a measurement between each data entry cluster generated by k-means clustering algorithm and a selected physiological data set and/or combination of genes, negative behaviors and/or negative behavioral propensities. Degree of similarity index value may indicate how close a particular fitness profile and/or recommended exercise is to being classified by k-means algorithm to a particular cluster. K-means clustering algorithm may evaluate the distances of the fitness profile and/or recommended exercise is to the k-number of clusters output by k-means clustering algorithm. Short distances between a fitness profile and/or recommended exercise and a cluster may indicate a higher degree of similarity between a fitness profile and/or recommended exercise and a particular cluster. Longer distances between a fitness profile and/or recommended exercise and a cluster may indicate a lower degree of similarity between a fitness profile and/or recommended exercise and a particular cluster.

With continued reference to FIG. 1, k-means clustering algorithm selects a classified data entry cluster as a function of the degree of similarity index value. In an embodiment, k-means clustering algorithm may select a classified data entry cluster with the smallest degree of similarity index value indicating a high degree of similarity between a fitness profile and/or recommended exercise and a particular data entry cluster. Alternatively or additionally k-means clustering algorithm may select a plurality of clusters having low degree of similarity index values to a fitness profile and/or recommended exercise, indicative of greater degrees of similarity. Degree of similarity index values may be compared to a threshold number indicating a minimal degree of relatedness suitable for inclusion of a fitness profile and/or recommended exercise in a cluster, where degree of similarity indices falling under the threshold number may be included as indicative of high degrees of relatedness. The above-described illustration of feature learning using k-means clustering is included for illustrative purposes only, and should not be construed as limiting potential implementation of feature learning algorithm; persons skilled in the art, upon reviewing the entirety of this disclosure, will be aware of various additional or alternative feature learning approaches that may be used consistently with this disclosure.

With continued reference to FIG. 1, computing device 104 generating a physical activity set 152 for a subject further comprises identifying at least a fitness activity contained within an activity profile. A "fitness activity," as used in this disclosure in any exercise, performance, task, or any other physical activity, that has been performed by the human subject as determined by the activity profile 112. Fitness activity may include one or more fitness suggestions for a user. Fitness suggestions may include particular exercises that a user should engage in, lengths of duration of particular exercises, intensity of exercises, frequency of exercise, and the like. Exercise may include the ability to practice and/or perform one or more sports, occupations, daily activities, mindfulness practices, breathing practices, relaxation practices, and the like, as discussed herein. For example, exercise may include a particular form of exercise such as cardiovascular exercise. Exercise may include a specific exercise such as running on a treadmill, climbing on a Stairmaster, practicing hatha yoga, walking in nature and the like. Computing device 104 may identify exercises contained within a activity profile 112. For example, an activity profile 112 may indicate that a user participates in a spinning class, prefers rock climbing, or has access to swimming daily. Computing device 104 may identify fitness activities contained within a activity profile 112.

Continuing in reference to FIG. 1, computing device 104 may query for the physical activity set associated with the fitness activity, wherein querying further comprises using the fitness machine-learning model 148 to generate a plurality of physical activities. Fitness machine-learning model 148 may train with training data the relates fitness activities found in the activity profile 112 data of subjects with physical activities 144. Fitness machine-learning model 148 may, alternatively or additionally, train with training data that corresponds to a plurality of data entries categories by a classifier that corresponds to human subject activity profile data for alike subjects, and the trained model may determine physical activity 144 that is compatible for the alike subjects. In this way, fitness machine-learning model 148 may accept input data from an activity profile 112 and generate an output of a plurality of physical activities 144. Computing device may then query for a physical activity sets based upon the physical activities generated by the model. As used in this disclosure, a "physical activity set" is at least a physical activity such as a suggested exercise, fitness action, and/or effort a subject may perform including additional information regarding frequency, periodicity, reps, exercise amounts, modifications and/or limitation to a physical activity, or any other physical activity data, that is tailored to a human subject based on their activity profile data. A physical activity set may include multiple physical activities 144. A physical activity set 152 may refer to a suggestion for a CrossFit-style workout, wherein a plurality of activities compatible for a subject may be combined with reps, timing, and a particular sequence, for instance stationary bike at 80% intensity for 3 km, followed by 1 minute rest, followed by push-ups, 3 sets of 25 push-ups with 30 seconds rest between sets, 3 sets of 30 kips, with 30 seconds between each set, and 3 sets of body planks for 30 seconds with 30 second rests. In such an example, fitness machine-learning model 148 may have identified fitness activities of biking, calisthenics, and a gauge of intermediate-level fitness in the activity profile 112 of the subject; whereas the computing device 104 may have taken those model outputs and used them as inputs to query for intermediate-level exercises that bridge calisthenics and biking and output the described physical activity set 152.

Continuing in reference to FIG. 1, computing device 104 may rank the plurality of physical activities, wherein ranking includes using a ranking machine-learning process to rank the plurality of physical activities as a function of how well the physical activity set matches to the at least a fitness activity. Ranking machine-learning process may be any machine-learning algorithm and/or process as performed by a machine-learning module, as described herein. Ranking machine-learning process may be the same type of algorithm as a classification machine-learning process 128 and/or fitness machine-learning model, as described above. Ranking machine-learning process may accept an input of a plurality of physical activities, including associated reps, time periods, daily schedules, weekly schedules, and the like, and generate an output which is ranked physical activities. Ranking may be performed as a function of a scoring function, wherein the rank is determined based on a variety of criteria, such as how well the physical activity matches the fitness level of the subject, as described herein. In such an example, the scoring function may be a statistical evaluation such as a confidence interval, or a probability that the physical activity set may be compatible with a particular activity profile 112.

Continuing in reference to FIG. 1, ranking machine-learning process 156 may include a statistical machine-learning process which may be a supervised and/or unsupervised machine-learning process, as described above. Alternatively or additionally, a statistical machine-learning process may be an online learning process, wherein an online machine learning process utilizes a method that, as data becomes available in a sequential order, the process is used to generate updated values that represent the best predictor for future data at each step. In online machine learning processes, whether applied in supervised and/or unsupervised learning, a function of $f: X \rightarrow Y$ is to be learned, wherein X is thought of as a space of inputs and Y as a space of outputs, and a prediction on the instances that may be drawn from a joint probability distribution, p(x,y), on X×Y. Machine-learning process may never determine the true distribution of p(x,y) over instances. Instead, the machine-learning process may access a training set of examples $(x_1,y_1), \ldots, (x_n,y_n)$. In this instance, a loss function may be given as $V:Y \times Y \rightarrow \mathbb{R}$, such that $V(f(x),y)$ measures the difference between the predicted value $f(x)$ and the true value, y. The ideal goal is to select a function $f \in \mathcal{H}$, where $\mathcal{H}$ is a space of functions called a 'hypothesis space', so that some notion of total loss is minimized. Depending on the type of model, such as a statistical model and/or an adversarial model, the statistical machine-learning process can devise different notions of loss, leading to different learning algorithms, and different variations of output values. In this example, the hypothesis space may be a set of physical activity sets, with exercise types, repetition-rest schemes, superset schemes, fitness difficulties, and combinations of each variable in a finite space such as 1-100 reps, 0 seconds to 360 seconds rest, novice to world-class difficulty, and the machine-learning process is calculating where the loss is minimized as the combination of variables most closely matches what is expected to recapitulate what is found in the activity profile data.

Statistical online machine learning process may use, for instance and without limitation, an empirical risk minimization, regularized empirical risk minimization, Tikhonov regularization, and the like, wherein the data in the training sample are assumed to have been drawn from a true distribution and the objective is to minimize the expected "risk" of a predicted value from the training sample, given some relationship between the predicted values and the training sample. In such examples, the choice of loss function may in minimization may be selected from a plurality of machine-learning algorithms such as regularized least squares analysis, linear least squares, stochastic gradient descent. Incremental stochastic gradient descent, batch learning, online convex optimization, support vector machines, and/or kernel methods. In a non-limiting illustrative example, any of the above algorithms may be performed by a ranking machine-learning process 156 wherein an input of a first set of values described by plurality of physical activity sets are input, and a set of information may be retrieved that describes a relationship, correlation, or other heuristic that relates a second predicted set of values related in some manner to the first set of values, for instance using a machine-learning model and/or classifier. In such an example, a ranking machine-learning process 156 may output a series of values that correspond to a physical activity set that represents predicted values that are statistically associated with a subject's past activity profile 112 data by use of an algorithm, as described above.

Statistical machine-learning process may be a reinforcement learning process, such as a Markov decision process (MDB), or the like. Reinforcement learning processes may be modeled as discrete-time stochastic control processes, wherein there exists a set of environment and agent states, S, a set of actions, A, of the agent, wherein $P_a(s, s') = Pr(s_{t+1}=s'|s_t=s, a_t=a)$ is the probability of transition, at time t, from state s to state s' under action, a. In such an example, the rules are often stochastic, in that numerical values may be randomly selected. It is assumed the agent may observe the current environment, or partially observe, wherein the set of actions is restricted, for instance, a numerical value of 0 may not be reduced below 0, for instance if the current value of the agent is 3, and the state transition reduces the value by 4, the transition will not be allowed, and an associated probability determined for the transition. In non-limiting illustrative examples, a reinforcement learning process may be utilized to determine the transition state of a particular set of values described in an activity profile 112 to generate final values that correspond to a physical activity set 152, wherein the transition is dictated by some predicted relationship between the activity profile 112 data and physical activity set 152. Likewise, in non-limiting illustrative examples, a reinforcement learning process may be used to determine predicted values of physical activity set 152 over long periods of time by optimizing a new state $s_{t+i}$ with a reward $r_{t+i}$ associated with the transition; for instance and without limitation the evolution of the physical activity set given a subject will pursue a first set of suggestions. The goal of the reinforcement learning agent is to collect as much reward as possible. The agent can choose any action, randomly or not, as a function of the history of values provided in prior physical activity set 152. In non-limiting illustrative examples, this may be performed to generate optimal predicted values of a second physical activity set 152 wherein the activity profile 112 data may not directly inform what the values should be, but may be used to optimally predict values for a long period, such as over the lifetime of a user.

Continuing in reference to FIG. 1, computing device 104 may select the at least a physical activity set as a function of the ranking. In non-limiting illustrative examples, computing device 104 may provide to the user a variety of ranked physical activity set outputs, for instance the top 10 ranked sets. In such an example, the user may select at least a physical activity set 152 as a function of the ranking that is display. The ranking may be provided as a variety of metrics, such as a statistical probability that the exercises could be currently completed by the subject. The ranking may be provided as a numerical value associated with the difficulty of completing the physical activity set according to how the set is statistically related to the current subject activity profile. The ranking may be provided as a percentile ranking of individuals with alike activity profile data as categorized by a classifier who indicated they enjoyed the physical activity sets.

Continuing in reference to FIG. 1, physical activity set 152 generated from the fitness machine-learning model 148 outputs and computing device 104 querying may impose one or more limitations or restrictions on a particular exercise. For example, physical activities generated may recommend a subject can engage in cardiovascular exercises that include running, jogging, and biking but subject cannot engage in spinning class because subjects heart rate has been too elevated every time user has engaged in spinning and one or more of subject's biological extractions indicate one or more genetic markers of heart disease.

Continuing in reference to FIG. 1, in yet another non-limiting example, physical activity set 152 may include one or more subject-specific modifications that indicate how user should modify a particular exercise or practice to best accommodate a user's needs and personal health. User specific modifications may allow a user to participate in a particular exercise but with modifications created based on one or more biological extractions and user health datums. For example, a user specific modification may indicate that a user should only engage in muscle strengthening exercise at most three days each week to avoid overtraining. In yet another non-limiting example, a user specific modification may indicate that a user can engage in yoga yina, vinyasa yoga, and hatha yoga but that the subject must modify handstand pose and instead perform child's pose because subject has carpel tunnel syndrome and a handstand pose would place excess stress on subject's joints. Or further, a subject may be able to engage in yoga, or any similar exercise, so long as the environment is not above room temperature, as higher temperatures may place a subject at risk for heat stroke, heart attack, nausea, dehydration, or other ailments. In yet another non-limiting example, a subject specific modification may include a suggestion that a subject should engage in one or more recommended exercise only after eating because subject's biological extractions indicate low fasting blood glucose levels upon waking.

Continuing in reference to FIG. 1, physical activity set 152 may also include data identifying physical activities that the subject should not engage in, or perhaps actively avoid. For instance and without limitation, recommended physical activity may indicate that a subject can engage in some weightlifting movements, such as bench press, push-ups, and bicep curls, but that a subject cannot engage in a leg press, squat, or calf extensions due to a recently torn calf muscle. In yet another non-limiting example, recommended exercise may indicate that a subject can engage in lighter-impact activities such as brisk walking, jogging, and playing golf, but that the subject cannot engage in upper body presses and/or swimming due to recent surgery on subject's rotator cuff.

With continued reference to FIG. 1, generating the at least a physical activity set 152 may include using the classification machine-learning process 128 to generate a classifier, wherein the classifier is used by the computing device 104 to filter physical activity sets 152. The classification machine-learning process 128 may filter out physical activity sets 152 based on the ranking associated with the physical activity set 152. In non-limiting illustrative examples, a plurality of physical activity sets 152 that rank relatively low due to increased difficulty relative to a subject's current fitness level may be classified in such a way that they are stored for later in the event a subject's fitness level increases. In further non-limiting illustrative examples, physical activity sets that rank low due to a current ailment, surgery, injury, or other temporary condition of a subject may be classified so that they may be stored and/or retrieved at some point in the future when a subject has recovered more completely.

Continuing in reference to FIG. 1, computing device 104 may generate, using a selected physical activity set, an physical activity instruction set, wherein the physical activity instruction set comprises instructions to implementing the selected physical activity set. An "physical activity instruction set" as used in this disclosure, is a set of one or more instructions to implementing one or more physical activity sets 152 suggested for a subject to engage in, wherein the steps of the instructions are uniquely generated to account for one or more elements of human subject data, including biological extraction data, activity profile data, and all other subject data described herein. Physical activity instruction set 160 may be generated by computing device utilizing any of the methodologies, as described above. Physical activity instruction set 160 may include information relayed to the subject regarding the way a physical activity set 152 was generated. Physical activity instruction set 160 may include information regarding timetables and schedules over short-term such as daily and weekly fitness regimens and/or long-term periods wherein the instruction set provides information to guide the user through an evolving physical activity set 152.

Continuing in reference to FIG. 1, computing device 104 may display a representation of the physical activity instruction set 160 via a graphical user interface. Computing device 104 may display physical activity instruction set 160 via a remote device, such as a "smartphone", laptop, tablet, and/or any other suitable device, as described in further detail below. Computing device 104 may display a representation of the physical activity instruction set 160 wherein the subject may be prompted to select instructions, or otherwise indicate that an instruction was followed and/or that an instruction served its purpose.

Figure 2:
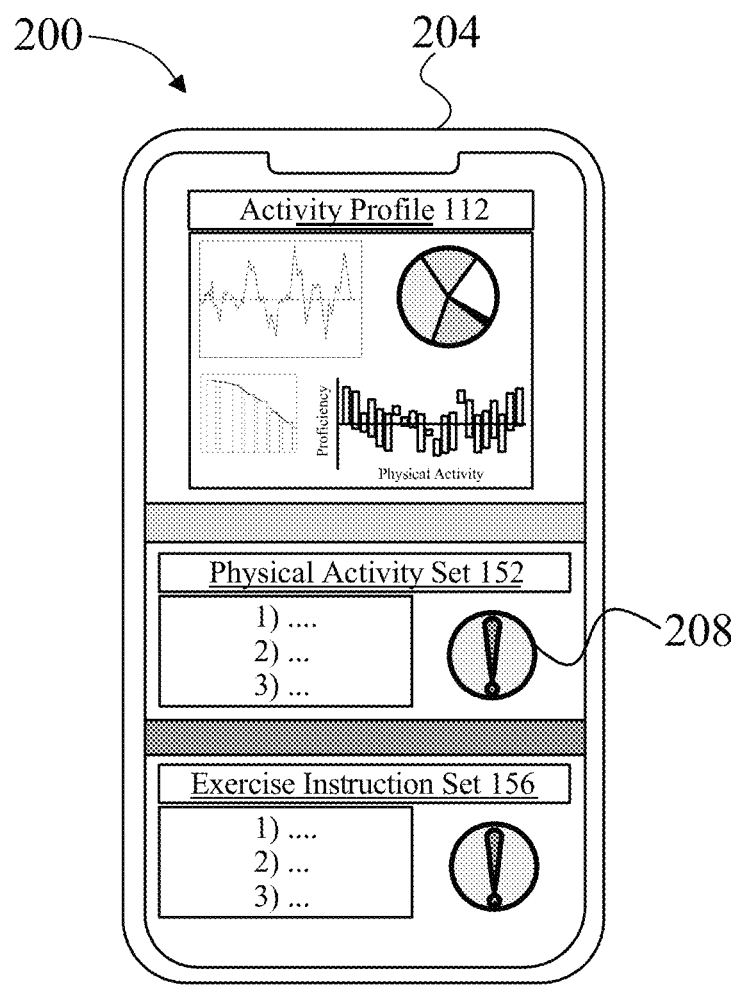
FIG. 2 is a diagrammatic representation of an exemplary embodiment of a remote device.

Referring now to FIG. 2, an exemplary embodiment 200 of a remote device 204 is illustrated. Computing device 104 may generate a presentation of the activity profile 112 and the at least a physical activity set 152 using a graphical user interface via the remote device 204. A "remote device," as used in this disclosure, is any user device such as a "smartphone", tablet, laptop, or any other suitable device with capability of presenting information via a graphical user interface. Remote device 204 may include a mobile phone operated by a subject or a computer or tablet operated by one of subject's informed advisors such as subject's fitness coach or health coach. Remote device 204 may provide the activity profile 112, physical activity set 152, physical activity instruction set 160, and/or any other data collected and generated herein. Remote device 204 may display a presentation using a graphical user interface (GUI) that may display graphics, text, audio, accept user inputs, commands, or the like, that allows the user to interact with electronic devices. Persons skilled in the art, upon review of the disclosure in its entirety, will be aware the various devices that may be used as a remote device and the ways in which information can be displayed via a graphical user interface.

Continuing in reference to FIG. 2, remote device 204 displaying via the graphical user interface is configured to accept human subject questionnaire data corresponding to at least a human subject activity and at least a physical activity set 152. As used in this disclosure, "human subject questionnaire data," is data that originates as input via a graphical user interface by a subject indicating a physical activity information after a remote device has prompted a subject for an input. Human subject questionnaire data 164 may include the type of physical activity, intensity, time spent engaging in activity, among other parameters. For instance and without limitation, Human subject questionnaire data 164 may be a subject's workout for the day, data from a wearable device such as the number of steps logged by a pedometer throughout the day, and the like. In non-limiting illustrative examples, remote device 204 may prompt a subject for Human subject questionnaire data 164 by providing a platform through the graphical user interface to input a textual submission. In further non-limiting illustrative examples, remote device 204 may prompt a subject for Human subject questionnaire data 164 by providing a drop-down menu to select a physical activity and associated data from a physical activity set 152. Remote device 204 may accept Human subject questionnaire data 164 as training data for a computing device 104 to use, as described above. For instance, Human subject questionnaire data 164 may be used with the activity machine-learning model 120 to generate an updated activity profile 112.

With continued reference to FIG. 2, system 100 may include a remote device 204. Remote device 204 may include without limitation, a display in communication with computing device 104, where a display may include any display as described herein. Remote device 204 may include an additional computing device, such as a mobile device, laptop, desktop, computer and the like. Remote device 204 may transmit and/or receive one or more inputs from computing device 104 utilizing any network methodology as described herein. Remote device 204 may be operated by a user which may include any human subject. Remote device 204 may be operated by an informed advisor. An "informed advisor" as used in this disclosure may include any health professional who may be responsible for organizing and/or delivering healthcare to a user. An informed advisor may include for example a functional medicine doctor, a yoga teacher, a reiki instructor, a psychologist, a nurse, a pharmacist, a dentist, a physician assistant, a nurse practitioner, a spiritual coach, a life coach, a health coach, a psychiatrist, a psychologist, and the like. Remote device 204 may transmit to computing device 104 one or more biological extractions to be stored in biological database 108. For instance and without limitation, remote device 204 may include a mobile phone operated by a user which may be utilized by the user to transmit blood test results that a user had analyzed at a recent appointment with the user's functional medicine physician. In yet another non-limiting example, remote device 204 may include a sensor that may track a user's heart rate during a yoga class which user may then transmit to computing device 104 to be stored in biological database 108. In yet another non-limiting example, remote device 204 may include a tablet operated by an informed advisor such as user's spiritual coach who may transmit one or more biological extractions obtained during a recent session between the user and the user's spiritual coach which may then be stored in biological database 108.

With continued reference to FIG. 2, system 100 may include a graphical user interface 28. Graphical user interface may include without limitation a form or other graphical element having data entry fields, wherein a user such as an expert may select one or more fields to enter one or more training sets. Graphical user interface may provide a drop-down menu where an expert may select a particular topic or category to enter a particular training set in relationship to. For instance and without limitation, an expert may have significant experience relating to particular forms of cardiovascular exercises best suited for individuals with high fasting blood glucose levels. In such an instance, expert may select a category displayed in a drop-down menu on graphical user interface to select an entry relating to biological extractions that include glucose levels. Graphical user interface may provide free form textual entry fields where an expert may enter one or more topics or categories that are of particular interest to an expert or that an expert has significant experience in treating and/or mitigating. Graphical user interface may also be utilized to display one or more outputs to a user such particular physical activity as described herein.

With continued reference to FIG. 2, computing device 104 may provide notifications during a human subject activity as a function of the human subject specific pattern. Computing device 104 may provide notifications via a remote device 204. A "notification," as used in this disclosure is a piece of information that alerts a subject to exertion. A notification 208 may be a textual alert, a graphic, a vibration alert, a sound, or any other audio-visual notification, or combination thereof, that a remote device 204 may provide a user. Persons skilled in the art, upon review of this disclosure in its entirety, will be aware of the various ways in which a remote device may provide notification to a subject.

Figure 3:
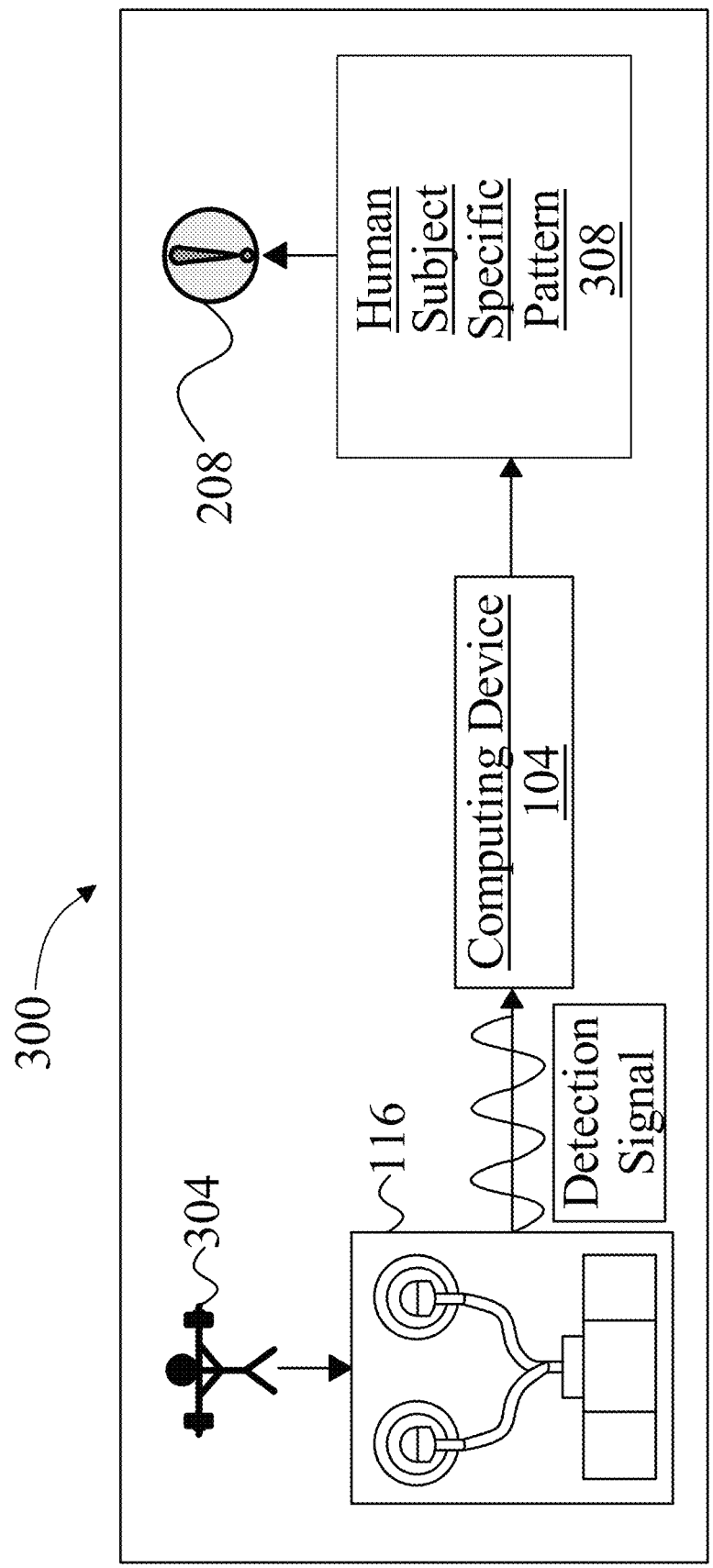
FIG. 3 is a diagrammatic representation of an exemplary embodiment of a computing device providing a notification as a function of the human subject specific pattern.

Referring now to FIG. 3, an exemplary embodiment 300 of computing device 104 providing a notification as a function of the human subject specific pattern is illustrated. A "human subject activity," as used in this disclosure, is any physical activity while being performed by a human subject in real-time. Computing device 104 may determine that a subject is engaging in a real-time human subject activity may be determined by a wearable device and/or sensor, as described herein, wherein human subject activity 304 is transmitted to computing device 104 during a task, exercise, or the like. A human subject activity 304 may be used as training data with a machine-learning model, as described above, while being collected by a computing device 104. For instance human subject activity 304 data may be accepted as an input by computing device 104 as signals from a sensor, and then be converted into an activity profile 112, as described above. A "human subject specific pattern," is an upper threshold of physical activity that is deemed safe for a subject to engage in, according to body measurements, disease state, physiological state, biological extraction data, and activity profile data. Human subject specific pattern 308 may be a threshold determined by computing device 104 based on biological extraction data, body measurements, disease state, or the like, where a computing device 104 may retrieve from, for instance an online database, a recommended healthy range of biological extraction data, physiological state data, and the like, that indicates a healthy range for a subject. In non-limiting illustrative examples, computing device 104 may retrieve information regarding safe heart rate range for a subject at particular age ranges, during particular exercises, with certain diseases, and the like. In such an example, when computing device 104 receive wearable fitness device 116 signals that indicate a heart rate above the healthy threshold, computing device 104 may alert a subject via a notification 208 that the human subject specific pattern 308 indicates the heart rate is above a healthy range, indicating exertion.

Figure 4:
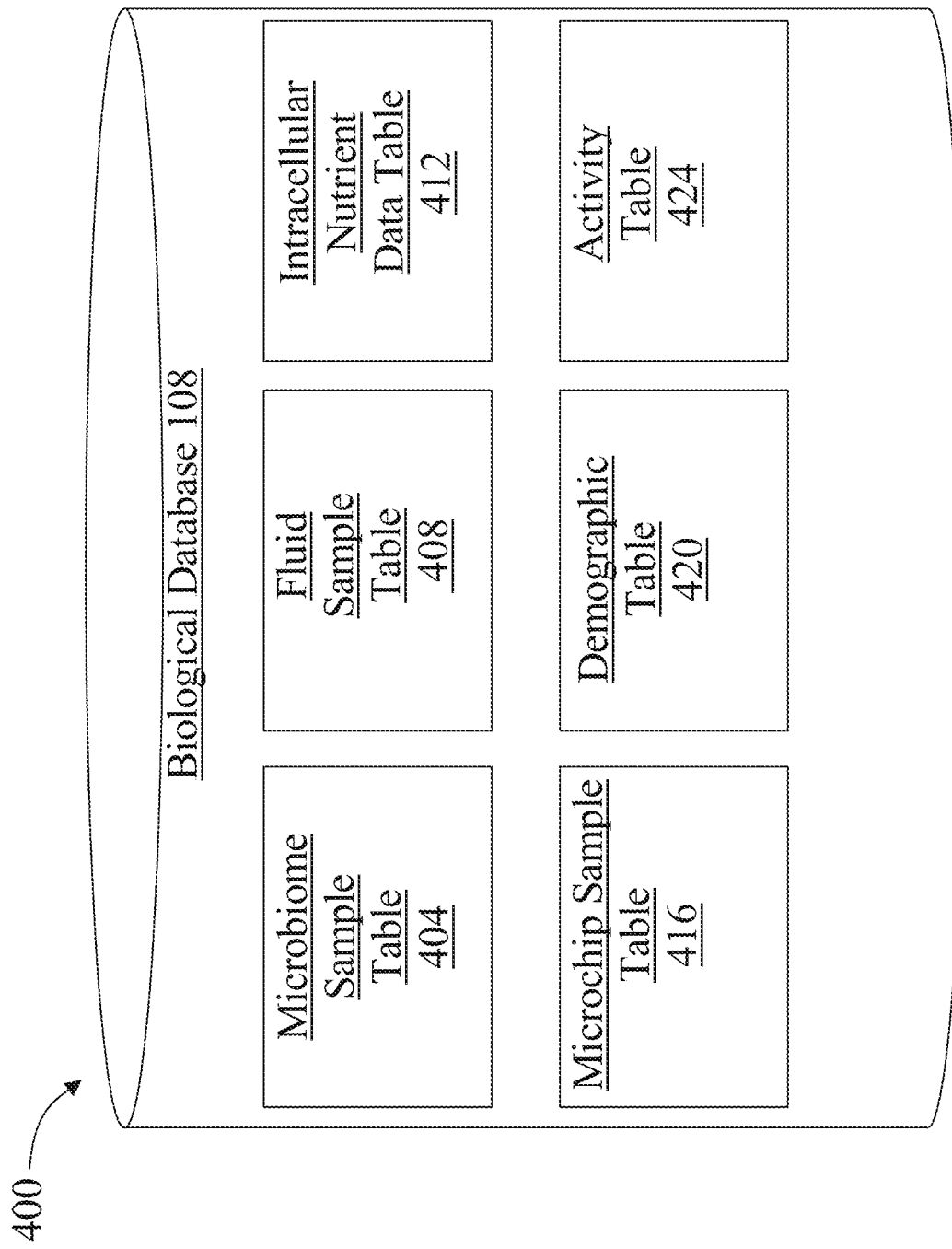
FIG. 4 is a block diagram illustrating an exemplary embodiment of a biological database.

Referring now to FIG. 4, an exemplary embodiment of biological database 108 is illustrated. Biological database 108 may be implemented as any data structure as described above. One or more tables contained within biological database 108 may include microbiome sample table 404; microbiome sample table 404 may include one or more biological extractions relating to the microbiome. For instance and without limitation, microbiome sample table 204 may include a physically extracted sample such as a stool sample analyzed for the presence of pathogenic species such as parasites and anaerobes. One or more tables contained within biological database 108 may include fluid sample table 408; fluid sample table 408 may include one or more biological extractions containing fluid samples. For instance and without limitation, fluid sample table 408 may include a urine sample analyzed for the presence or absence of glucose. One or more tables contained within biological database 108 may include intracellular nutrient data table 412; intracellular nutrient data table 412 may include one or more biological extractions containing intracellular nutrient levels. For instance and without limitation, intracellular nutrient data table 412 may include a blood sample analyzed for intracellular levels of Vitamin B12. One or more tables contained within biological database 108 may include microchip sample table 416; microchip sample table 416 may include one or more biological extractions obtained from a microchip. For instance and without limitation, microchip sample table 416 may include a blood sugar level obtained from a microchip embedded under a user's skin. One or more tables contained within biological database 108 may include demographic table 420; demographic table 420 may include one or more demographic inputs pertaining to a user. For instance and without limitation, demographic table 420 may include information pertaining to a user's full name, address, date of birth, sex, marital status, occupation, and the like. One or more tables contained within biological database 108 may include activity table 424; activity table 424 may include one or more elements of user activity data. For instance and without limitation, activity table 424 may include a description of one or more exercises that a user participates in, and/or one or more elements of user activity data.

Figure 5:
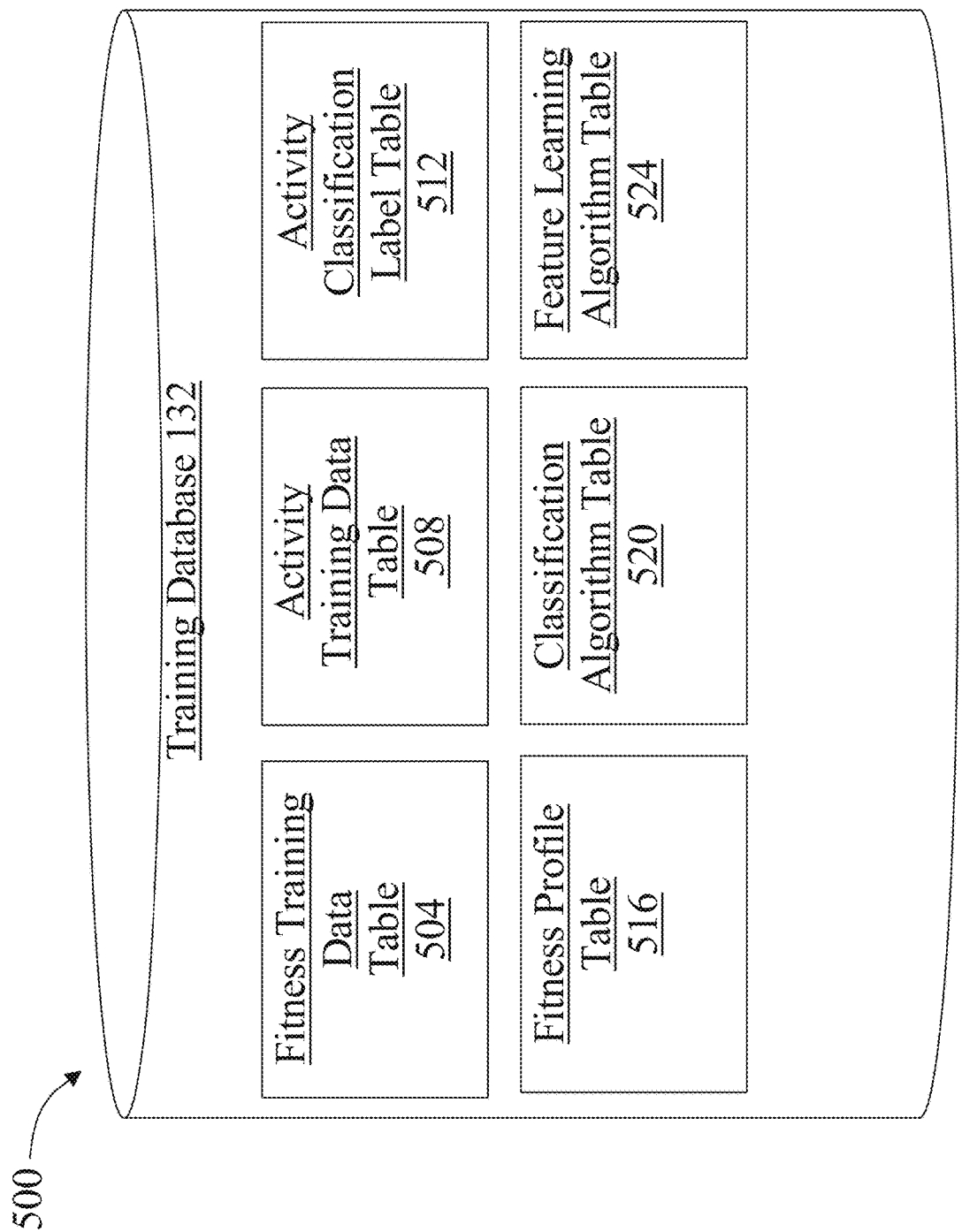
FIG. 5 is a block diagram illustrating an exemplary embodiment of a training database.

Referring now to FIG. 5, an exemplary embodiment of training database 132 is illustrated. Training database 132 may be implemented as any data structure suitable for use as biological database 108 as described above in more detail in FIG. 1. One or more tables contained within training database 132 may include fitness training data table 504; fitness training data table 304 may include one or more training data 124 sets. One or more tables contained within training database 132 may include activity training data table 508; activity training data table 508 may include one or more activity training data sets. One or more tables contained within training database 132 may include activity classification label table 312; activity classification label table 312 may include one or more activity training data sets containing activity classification labels and/or stored in training database 132 by activity classification label. One or more tables contained within training database 132 may include fitness profile table 516; fitness profile table 516 may include one or more fitness profiles and/or one or more suggested training sets to be selected and utilized for one or more fitness profiles. One or more tables contained within training database 132 may include classification algorithm table 520; classification algorithm table 520 may include one or more Classification machine-learning process 128. In an embodiment, one or more Classification machine-learning process 128 contained within classification algorithm table 520 may be previously calculated and loaded into training database 132 thereby being able to be utilized to generate an output by computing device 104 more rapidly. One or more tables contained within training database 132 may include feature learning algorithm table 524; feature learning algorithm table 524 may include one or more feature learning algorithm 152. In an embodiment, one or more feature learning algorithm 152 contained within feature learning algorithm table 524 may be previously calculated and loaded into training database 132 thereby being able to be utilized to generate an output by computing device 104 more rapidly.

Figure 6:
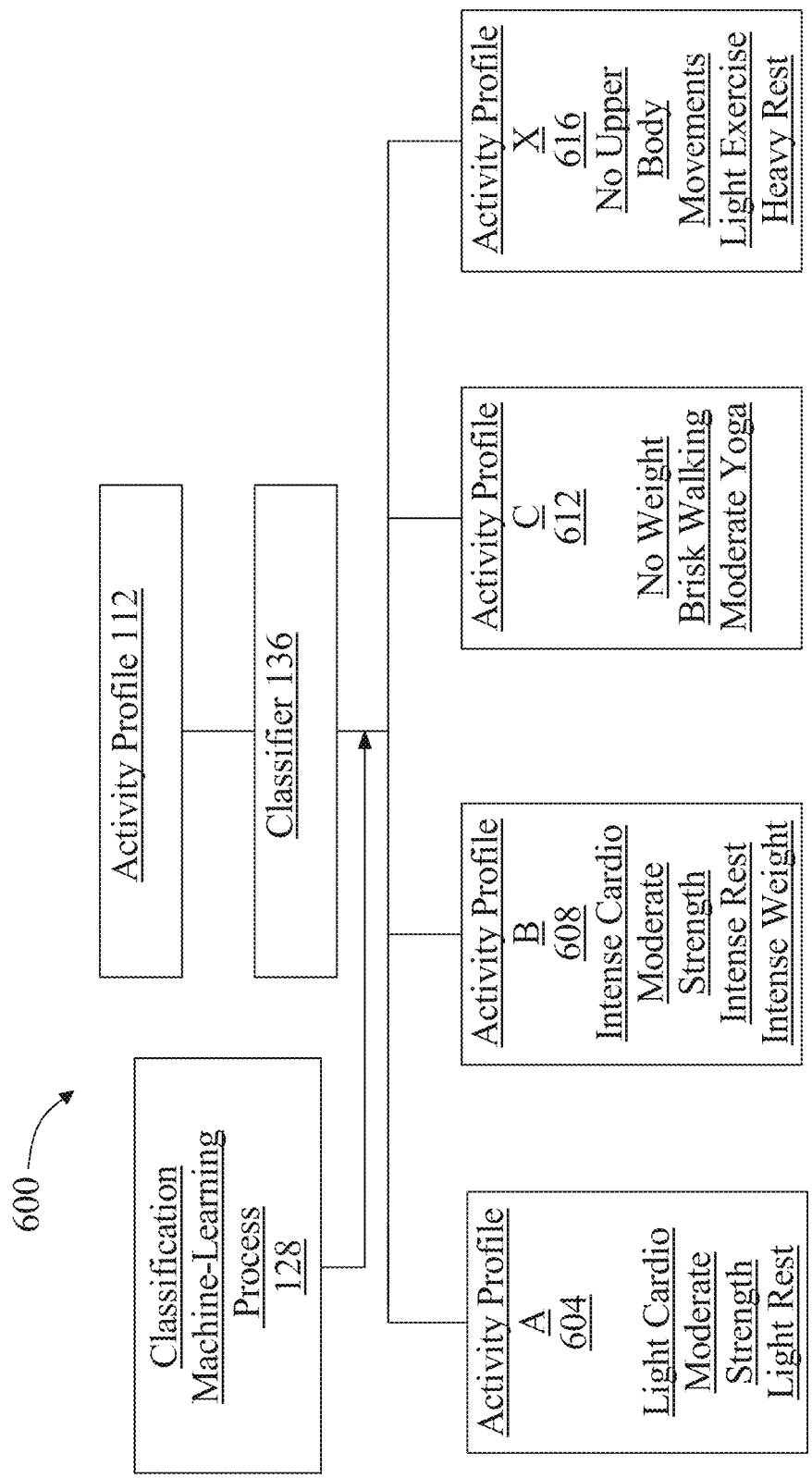
FIG. 6 is a block diagram illustrating an exemplary embodiment of a classifier.

Referring now to FIG. 6, an exemplary embodiment 600 of classifier 136 is illustrated. Classifier 136 may be generated by computing device 104 utilizing any of the methodologies as described above. Classifier 136 receives activity profile 112 from biological database 108 as described above. Activity profile 112 includes a biological extraction and at least an element of user activity data. Classifier 136 classifies using a Classification machine-learning process 128 an activity profile 112 as an input and outputs a fitness profile. Classification machine-learning process 128 includes any of the Classification machine-learning process 128 as described above. Fitness profile includes any of the fitness profiles as described above. Fitness profile includes a preferred fitness level. Classifier 136 may take into account additional factors beyond activity profile 112 when using a Classification machine-learning process 128 to output a fitness profile. Classifier 136 may output a fitness profile by evaluating a user's age, sex, demographic information, and/or any other information that may be relevant pertaining to what exercises and/or routines that a user may or may not be able to perform. For example, classifier 136 may not output a fitness profile that contains any exercises that utilize upper body strength and arm movement if a user has a broken shoulder. In yet another non-limiting example, classifier 136 may not output a fitness profile that contains intense cardiovascular exercise for a user who recently suffered a heart attack. Classifier 136 may take into account additional factors when necessary based on expert input. Expert input includes any of the expert input as described above.

With continued reference to FIG. 6, classifier 136 selects an activity profile 112. In an embodiment, activity profile A 604 may include a description of one or more exercises contained within the fitness profile A such as light cardio, moderate strength, and light rest. In an embodiment, activity profile B 608 may include intense cardio, moderate strength, intense rest, and intense weight. In an embodiment, activity profile C 612 may include no weights, brisk walking, and moderate yoga. Classification machine-learning process 128 may aid classifier 136 in selecting a fitness profile from activity profile X 616 or an indefinite number of fitness profiles. Selection of a particular Classification machine-learning process 128 that classifier 136 may utilize to select a particular fitness profile may be contained within training database 132 as described above and may be based on expert input.

Figure 7:
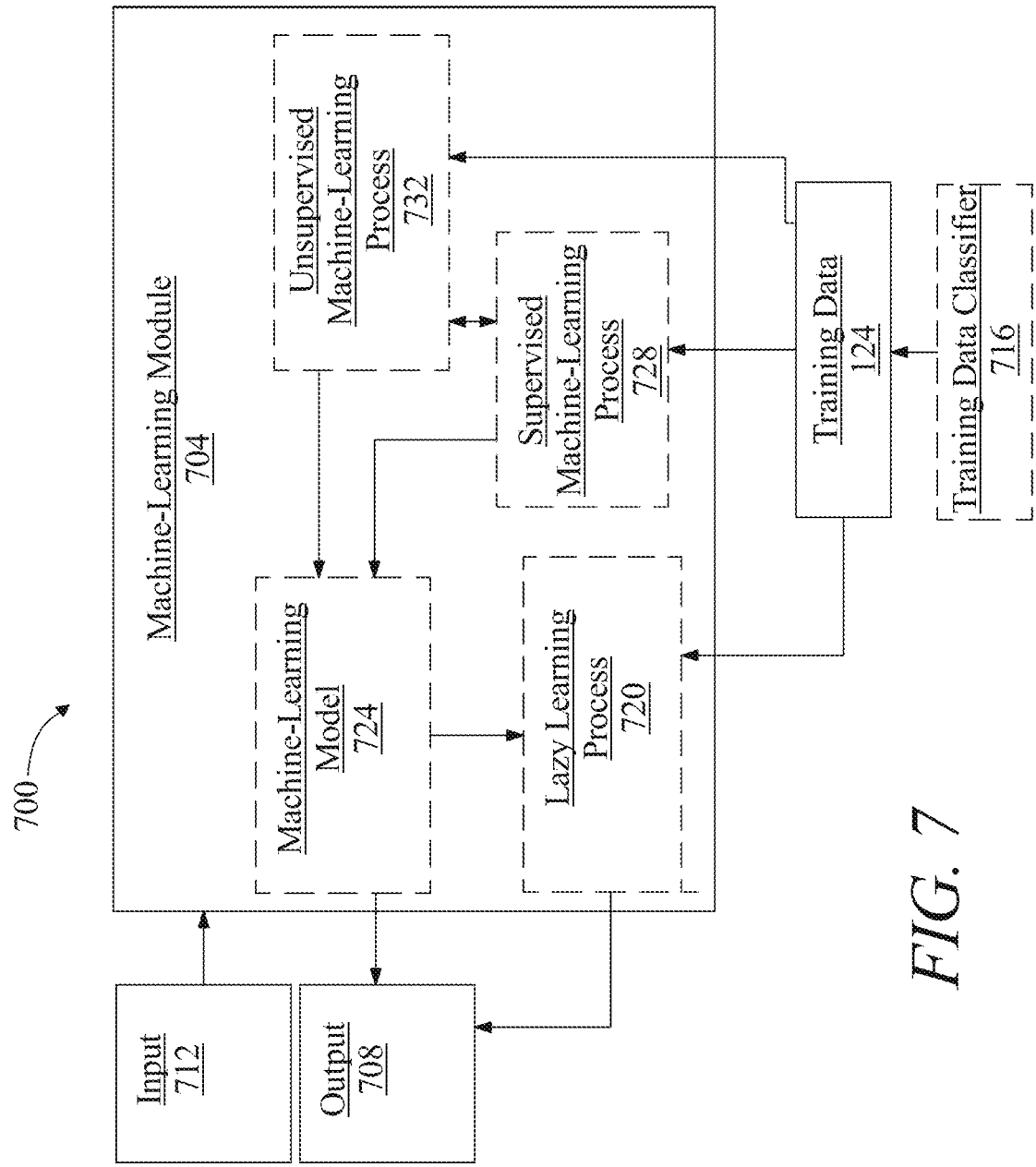
FIG. 7 is a block diagram illustrating an exemplary embodiment of a machine-learning module.

Referring now to FIG. 7, an exemplary embodiment 700 of a machine-learning module 704 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 124 to generate an algorithm that will be performed by a computing device/module to produce outputs 708 given data provided as inputs 712; this is in contrast to a non-machine learning software program where the commands to be executed are determined in advance by a user and written in a programming language.

Still referring to FIG. 7, "training data," as used herein, is data containing correlations that a machine-learning process may use to model relationships between two or more categories of data elements. For instance, and without limitation, training data 704 may include a plurality of data entries, each entry representing a set of data elements that were recorded, received, and/or generated together; data elements may be correlated by shared existence in a given data entry, by proximity in a given data entry, or the like. Multiple data entries in training data 704 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 704 according to various correlations; correlations may indicate causative and/or predictive links between categories of data elements, which may be modeled as relationships such as mathematical relationships by machine-learning processes as described in further detail below. Training data 704 may be formatted and/or organized by categories of data elements, for instance by associating data elements with one or more descriptors corresponding to categories of data elements. As a non-limiting example, training data 704 may include data entered in standardized forms by persons or processes, such that entry of a given data element in a given field in a form may be mapped to one or more descriptors of categories. Elements in training data 704 may be linked to descriptors of categories by tags, tokens, or other data elements; for instance, and without limitation, training data 704 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 7, training data 704 may include one or more elements that are not categorized; that is, training data 704 may not be formatted or contain descriptors for some elements of data. Machine-learning algorithms and/or other processes may sort training data 704 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 704 to be made applicable for two or more distinct machine-learning algorithms as described in further detail below. Training data 704 used by machine-learning module 700 may correlate any input data as described in this disclosure to any output data as described in this disclosure. As a non-limiting illustrative example a plurality of entries correlating human subject signals to a plurality of human subject activity metrics and outputs of an activity profile 112.

Further referring to FIG. 7, training data may be filtered, sorted, and/or selected using one or more supervised and/or unsupervised machine-learning processes and/or models as described in further detail below; such models may include without limitation a training data classifier 716. A "training data classifier" may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 704 may generate a classifier using a classification algorithm, defined as a processes whereby a computing device and/or any module and/or component operating thereon derives a classifier from training data 124. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 716 may classify elements of training data to [something that characterizes a sub-population, such as a cohort of persons and/or other analyzed items and/or phenomena for which a subset of training data may be selected].

Still referring to FIG. 7, machine-learning module 700 may be configured to perform a lazy-learning process 720 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 704. Heuristic may include selecting some number of highest-ranking associations and/or training data 704 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 7, machine-learning processes as described in this disclosure may be used to generate machine-learning models 724. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 724 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 724 may be generated by creating an artificial neural network, such as a convolutional neural network comprising an input layer of nodes, one or more intermediate layers, and an output layer of nodes. Connections between nodes may be created via the process of "training" the network, in which elements from a training data 704 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 7, machine-learning algorithms may include at least a supervised machine-learning process 728. At least a supervised machine-learning process 728, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include [input examples] as described above as inputs, [output examples] as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 704. Persons skilled in the art, upon reviewing the entirety of this disclosure, will be aware of various possible variations of at least a supervised machine-learning process 728 that may be used to determine relation between inputs and outputs. Supervised machine-learning processes may include classification algorithms as defined above.

Further referring to FIG. 7, machine learning processes may include at least an unsupervised machine-learning processes 732. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 7, machine-learning module 700 may be designed and configured to create a machine-learning model 724 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 7, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 7, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data 124 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data 704.

Figure 8:
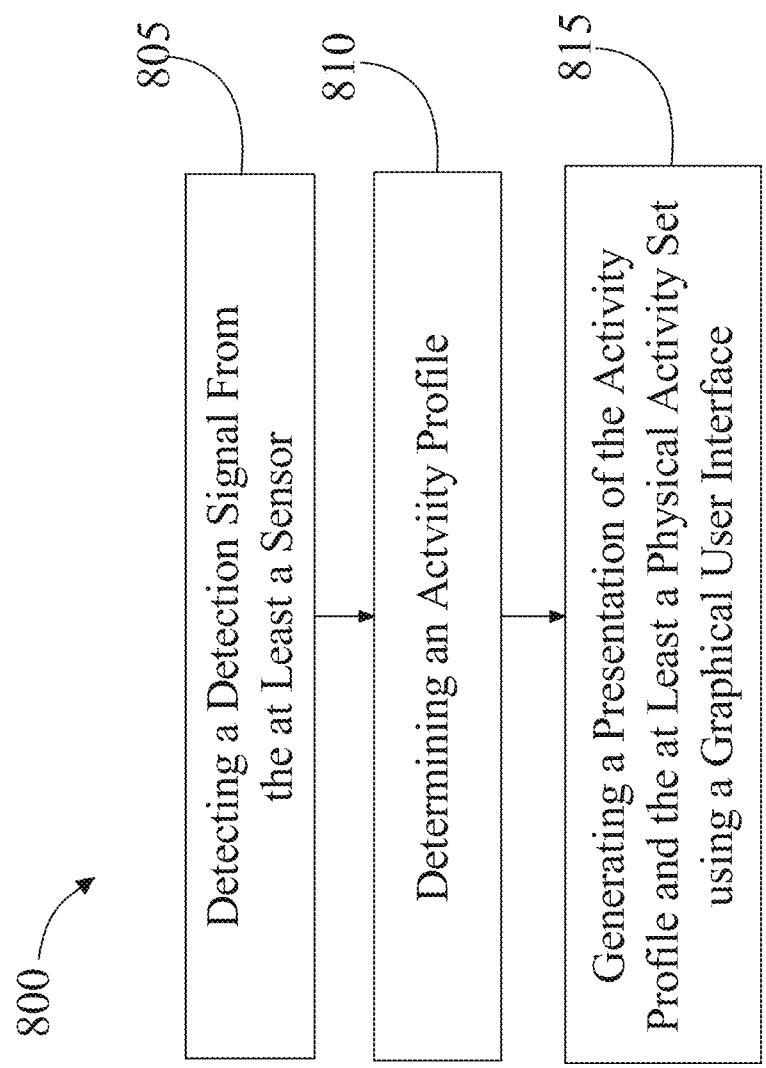
FIG. 8 is a process flow diagram illustrating an exemplary embodiment of a method for generating physical activity sets for a human subject.

Referring now to FIG. 8, a method 800 for generating physical activity sets for a human subject is illustrated. At step 805, computing device 104 is configured for detecting a signal from the at least a wearable fitness device. At least a wearable fitness device includes a sensor; this may be implemented, without limitation, as described above in FIG. 1-6.

Continuing in reference to FIG. 8, at step 810, computing device 104 is configured for determining an activity profile 112, wherein determining the activity profile 112 includes generating an activity machine-learning model 120, wherein the activity machine-learning model 120 is trained with training data 124 that includes a plurality of entries and each entry correlates human subject signal to a plurality of human subject activity metrics, determining, using the activity machine-learning model 120 and the signal, the activity profile 112, generating, using the activity profile 112, at least a physical activity set wherein generating at least a physical activity set includes classifying the activity profile 112 with corresponding activity profile data from a plurality of human subjects, wherein the corresponding activity profile 112 data correlates activity profile 112 data to at least a physical activity set 152, training a fitness machine-learning model 148 using the corresponding activity profile 112 data, and generating the at least a physical activity set 152 as a function of the activity profile 112 data and the fitness machine-learning model 148; this may be implemented, without limitation, as described above in FIG. 1-6.

Still referring to FIG. 8, continuing at step 810, computing device 104 is configured to classify, using a classification machine-learning process 128, the signal to at least an element of human subject data. Computing device 104 is configured to provide a real-time fitness update 140 during a human subject activity using reactive computing, wherein the real-time fitness update 140 is provided as a change in an element of human subject data of a human subject during collection of the signal. Providing the real-time fitness update 140 includes storing the real-time fitness update 140 in a database; this may be implemented, without limitation, as described above in FIG. 1-6.

Still referring to FIG. 8, continuing at step 810, graphical user interface is configured to accept human subject questionnaire data corresponding to at least a human subject activity and at least a physical activity set 152. Computing device 104 is configured to provide notifications during a human subject activity as a function the human subject specific pattern.

Still referring to FIG. 8, continuing at step 810, selecting the at least a physical activity set 152 for the human subject includes identifying at least a fitness activity contained within an activity profile 112, querying for the physical activity set 152 associated with the fitness activity, wherein querying includes using the fitness machine-learning model 148 to generate a plurality of physical activity sets 152, ranking the plurality of physical activity sets 152, wherein ranking includes using a ranking machine-learning process 156 to rank at least a physical activity set as a function of how well the physical activity set matches to the at least a fitness activity, and selecting the at least a physical activity set as a function of the ranking.

Still referring to FIG. 8, continuing at step 810, generating, using a selected physical activity set 152, an physical activity instruction set 160, wherein the physical activity instruction set 160 includes instructions to implementing the selected physical activity set 152, and displaying a representation of the physical activity instruction set via a graphical user interface. Selecting the at least a physical activity set 152 includes using the classification machine-learning process 128 to generate a classifier 136, wherein the classifier 136 is used by the computing device 104 to filter physical activity sets 152.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 9:
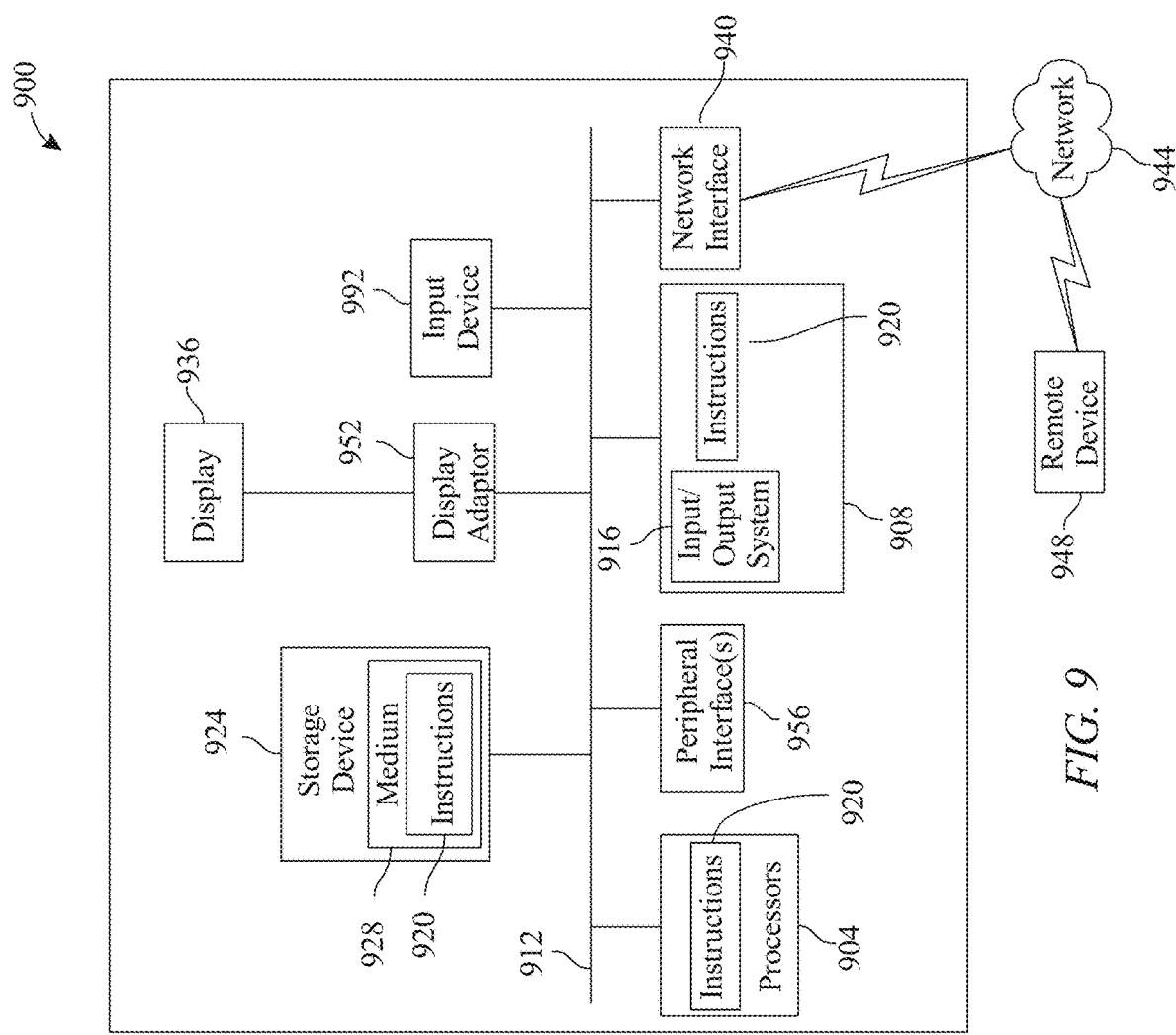
FIG. 9 is a block diagram of a computing system that can be used to implement any one or more of the methodologies disclosed herein and any one or more portions thereof.

FIG. 9 shows a diagrammatic representation of one embodiment of a computing device in the exemplary form of a computer system 900 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 900 includes a processor 904 and a memory 908 that communicate with each other, and with other components, via a bus 912. Bus 912 may include any of several types of bus structures including, but not limited to, a memory bus, a memory controller, a peripheral bus, a local bus, and any combinations thereof, using any of a variety of bus architectures.

Processor 904 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 904 may be organized according to Von Neumann and/or Harvard architecture as a non-limiting example. Processor 904 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 908 may include various components (e.g., machine-readable media) including, but not limited to, a random-access memory component, a read only component, and any combinations thereof. In one example, a basic input/output system 916 (BIOS), including basic routines that help to transfer information between elements within computer system 900, such as during start-up, may be stored in memory 908. Memory 908 may also include (e.g., stored on one or more machine-readable media) instructions (e.g., software) 920 embodying any one or more of the aspects and/or methodologies of the present disclosure. In another example, memory 908 may further include any number of program modules including, but not limited to, an operating system, one or more application programs, other program modules, program data, and any combinations thereof.

Computer system 900 may also include a storage device 924. Examples of a storage device (e.g., storage device 924) include, but are not limited to, a hard disk drive, a magnetic disk drive, an optical disc drive in combination with an optical medium, a solid-state memory device, and any combinations thereof. Storage device 924 may be connected to bus 912 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 924 (or one or more components thereof) may be removably interfaced with computer system 900 (e.g., via an external port connector (not shown)). Particularly, storage device 924 and an associated machine-readable medium 928 may provide nonvolatile and/or volatile storage of machine-readable instructions, data structures, program modules, and/or other data for computer system 900. In one example, software 920 may reside, completely or partially, within machine-readable medium 928. In another example, software 920 may reside, completely or partially, within processor 904.

Computer system 900 may also include an input device 932. In one example, a user of computer system 900 may enter commands and/or other information into computer system 900 via input device 932. Examples of an input device 932 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 932 may be interfaced to bus 912 via any of a variety of interfaces (not shown) including, but not limited to, a serial interface, a parallel interface, a game port, a USB interface, a FIRE-WIRE interface, a direct interface to bus 912, and any combinations thereof. Input device 932 may include a touch screen interface that may be a part of or separate from display 936, discussed further below. Input device 932 may be utilized as a user selection device for selecting one or more graphical representations in a graphical interface as described above.

A user may also input commands and/or other information to computer system 900 via storage device 924 (e.g., a removable disk drive, a flash drive, etc.) and/or network interface device 940. A network interface device, such as network interface device 940, may be utilized for connecting computer system 900 to one or more of a variety of networks, such as network 944, and one or more remote devices 948 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 944, may employ a wired and/or a wireless mode of communication. In general, any network topology may be used. Information (e.g., data, software 920, etc.) may be communicated to and/or from computer system 900 via network interface device 940.

Computer system 900 may further include a video display adapter 952 for communicating a displayable image to a display device, such as display device 936. Examples of a display device include, but are not limited to, a liquid crystal display (LCD), a cathode ray tube (CRT), a plasma display, a light emitting diode (LED) display, and any combinations thereof. Display adapter 952 and display device 936 may be utilized in combination with processor 904 to provide graphical representations of aspects of the present disclosure. In addition to a display device, computer system 900 may include one or more other peripheral output devices including, but not limited to, an audio speaker, a printer, and any combinations thereof. Such peripheral output devices may be connected to bus 912 via a peripheral interface 956. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating physical activity sets for a human subject, the system comprising:
   a computing device configured to:
   detect a signal from at least a wearable fitness device;
   determine an activity profile, wherein determining the activity profile further comprises;
      generating an activity machine-learning model, wherein the activity machine-learning model is trained with training data that includes a plurality of entries and each entry correlates human subject signals to a plurality of human subject activity metrics; and
      determining, using the activity machine-learning model and the signal, the activity profile;
   generate, using the activity profile, at least a physical activity set wherein generating the at least a physical activity set further comprises:
      classifying the activity profile to corresponding activity profile data from a plurality of human subjects, wherein the corresponding activity profile data correlates activity profile data to at least a physical activity;
      training a fitness machine-learning model using the corresponding activity profile data; and
      generating the at least a physical activity set as a function of the activity profile data and the fitness machine-learning model; and
   present the activity profile and the at least a physical activity set using a graphical user interface.

2. The system of claim 1, wherein at least a wearable fitness device includes a sensor.

3. The system of claim 2, wherein the computing device is configured to classify, using a classification machine-learning process, the signal to at least an element of human subject data.

4. The system of claim 1, wherein the computing device is configured to provide a real-time fitness update during a human subject activity using reactive computing, wherein the real-time fitness update is provided as a change in an element of human subject data of a human subject during collection of the signal.

5. The system of claim 4, wherein providing the real-time fitness update further comprises storing the real-time fitness update in a database.

6. The system of claim 1, wherein generating the at least a physical activity set for the human subject further comprises:
   identifying at least a fitness activity contained within an activity profile; and generating a plurality of physical activities as a function of the fitness machine-leaning model and the at least a fitness activity;

ranking the plurality of physical activities, wherein ranking further comprises using a ranking machine-learning process to rank the plurality of physical activities as a function of how well the physical activity set matches to the at least a fitness activity; and selecting the at least a physical activity set as a function of the ranking.

7. The system of claim 1, wherein generating the at least a physical activity set further comprises:

generating a classifier as a function of a classification machine-learning process; and filtering a plurality of physical activities as a function of the classifier.

8. The system of claim 1 further comprising:

generating, using the at least a physical activity set, a physical activity instruction set, wherein the physical activity instruction set comprises instructions to implementing the at least a physical activity set; and displaying a representation of the physical activity instruction set via a graphical user interface.

9. The system of claim 1, wherein the graphical user interface is configured to accept human subject questionnaire data corresponding to at least a human subject activity and at least a physical activity set.

10. The system of claim 1, wherein the computing device is further configured to provide notifications during a human subject activity as a function of the human subject specific pattern.

11. A method for generating physical activity sets for a human subject, the method comprising:

a computing device configured for:

detecting a signal from the at least a wearable fitness device;

determining an activity profile, wherein determining the activity profile further comprises;

generating an activity machine-learning model, wherein the activity machine-learning model is trained with training data that includes a plurality of entries and each entry correlates human subject signal to a plurality of human subject activity metrics;

determining, using the activity machine-learning model and the signal, the activity profile;

generating, using the activity profile, at least a physical activity set wherein generating at least a physical activity set further comprises:

classifying the activity profile to corresponding activity profile data from a plurality of human subjects, wherein the corresponding activity profile data correlates activity profile data to at least a physical activity set;

training a fitness machine-learning model using the corresponding activity profile data; and generating the at least a physical activity set as a function of the activity profile data and the fitness machine-learning model; and presenting the activity profile and the at least a physical activity set using a graphical user interface.

12. The method of claim 11, wherein at least a wearable fitness device includes a sensor.

13. The method of claim 12, wherein the computing device is configured to classify, using a classification machine-learning process, the signal to at least an element of human subject data.

14. The method of claim 11, wherein the computing device is configured to provide a real-time fitness update during a human subject activity using reactive computing, wherein the real-time fitness update is provided as a change in an element of human subject data of a human subject during collection of the signal.

15. The method of claim 14, wherein providing the real-time fitness update further comprises storing the real-time fitness update in a database.

16. The method of claim 11, wherein the graphical user interface is configured to accept human subject questionnaire data corresponding to at least a human subject activity and at least a physical activity set.

17. The method of claim 11, wherein the computing device is further configured to provide notifications during a human subject activity as a function the human subject specific pattern.

18. The method of claim 11, wherein selecting the at least a physical activity set for the human subject further comprises:

identifying at least a fitness activity contained within an activity profile; and querying for the physical activity set associated with the fitness activity, wherein querying further comprises using the fitness machine-learning model to generate a plurality of physical activity sets;

ranking the plurality of physical activity set, wherein ranking further comprises using a ranking machine-learning process to rank at least a physical activity set as a function of how well the physical activity set matches to the at least a fitness activity; and selecting the at least a physical activity set as a function of the ranking.

19. The method of claim 11 further comprising:

generating, using a selected physical activity set, a physical activity instruction set, wherein the physical activity instruction set comprises instructions to implementing the selected physical activity set; and displaying a representation of the physical activity instruction set via a graphical user interface.

20. The method of claim 11, wherein selecting the at least a physical activity set further comprises using the classification machine-learning process to generate a classifier, wherein the classifier is used by the computing device to filter physical activity set.

* * * * *